(12) United States Patent
Simmons et al.

(10) Patent No.: US 9,688,775 B2
(45) Date of Patent: Jun. 27, 2017

(54) SYSTEM FOR ANTIBODY EXPRESSION AND ASSEMBLY

(71) Applicant: Genentech, Inc., South San Francisco, CA (US)

(72) Inventors: Laura Simmons, Burlingame, CA (US); Dana Andersen, Redwood City, CA (US)

(73) Assignee: GENENTECH, INC., South San Francisco, CA (US)

( * ) Notice: Subject to any disclaimer, the term of this patent is extended or adjusted under 35 U.S.C. 154(b) by 127 days.

(21) Appl. No.: 14/019,399

(22) Filed: Sep. 5, 2013

(65) Prior Publication Data

US 2014/0120580 A1 May 1, 2014

Related U.S. Application Data

(63) Continuation of application No. 13/033,521, filed on Feb. 23, 2011, now abandoned, which is a continuation of application No. 11/438,484, filed on May 22, 2006, now abandoned, which is a continuation of application No. 11/351,886, filed on Feb. 9, 2006, now abandoned, which is a continuation of application No. 10/227,694, filed on Aug. 26, 2002, now abandoned.

(60) Provisional application No. 60/315,209, filed on Aug. 27, 2001.

(51) Int. Cl.
| | |
|---|---|
| *C12P 21/02* | (2006.01) |
| *C12P 21/08* | (2006.01) |
| *C07K 16/36* | (2006.01) |
| *C07K 16/00* | (2006.01) |
| *C07K 16/28* | (2006.01) |
| *C12N 15/13* | (2006.01) |
| *C12N 15/63* | (2006.01) |
| *C12N 15/67* | (2006.01) |
| *C12N 15/70* | (2006.01) |

(52) U.S. Cl.
CPC .............. *C07K 16/36* (2013.01); *C07K 16/00* (2013.01); *C07K 16/2845* (2013.01); *C07K 16/2896* (2013.01); *C07K 2317/54* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,816,567 A | 3/1989 | Cabilly et al. |
| 4,927,762 A | 5/1990 | Darfler |
| 5,122,469 A | 6/1992 | Mather et al. |
| 5,208,020 A | 5/1993 | Chari et al. |
| 5,264,365 A | 11/1993 | Georgiou et al. |
| 5,500,362 A | 3/1996 | Robinson et al. |
| 5,508,192 A | 4/1996 | Georgiou et al. |
| 5,585,097 A | 12/1996 | Bolt et al. |
| 5,624,821 A | 4/1997 | Winter et al. |
| 5,639,635 A | 6/1997 | Joly et al. |
| 5,641,870 A | 6/1997 | Rinderknecht et al. |
| 5,648,237 A | 7/1997 | Carter |
| 5,648,260 A | 7/1997 | Winter et al. |
| 5,693,493 A | 12/1997 | Robinson et al. |
| 5,747,662 A | 5/1998 | Simmons et al. |
| 5,821,337 A | 10/1998 | Carter et al. |
| 5,840,523 A | 11/1998 | Simmons et al. |
| 6,008,023 A | 12/1999 | Opper et al. |
| 6,027,888 A | 2/2000 | Georgiou et al. |
| 6,083,715 A | 7/2000 | Georgiou et al. |
| 6,171,586 B1 | 1/2001 | Lam et al. |
| 6,284,488 B1 | 9/2001 | Weir et al. |
| 6,312,690 B1 | 11/2001 | Edelman et al. |
| 6,331,415 B1 | 12/2001 | Cabilly et al. |
| 6,455,279 B1 | 9/2002 | Ambrosius et al. |
| 6,468,738 B1 | 10/2002 | Kang et al. |
| 6,602,688 B1 | 8/2003 | Opper et al. |
| 6,828,121 B2 | 12/2004 | Chen |
| 6,979,556 B2 | 12/2005 | Simmons et al. |
| 2002/0037558 A1 | 3/2002 | Lo et al. |
| 2003/0073164 A1 | 4/2003 | Simmons et al. |
| 2003/0119075 A1 | 6/2003 | Kirchhofer et al. |
| 2004/0126807 A1 | 7/2004 | Goddard et al. |

(Continued)

FOREIGN PATENT DOCUMENTS

| | | |
|---|---|---|
| EP | 0 154 316 B1 | 9/1985 |
| EP | 0 324 162 A1 | 12/1988 |

(Continued)

OTHER PUBLICATIONS

Arie et al. (2001). "Chaperone Function of FkpA, a Heat Shock Prolyl Isomerase, in the Periplasm of *Escherichia coli*," *Molecular Microbiology* 39(1):199-210.
Armour et al. (1999). "Recombinant Human IgG Molecules Lacking FCγ Receptor I Binding and Monocyte Triggering Activities", *Eur. J. Immunol.* 29:2613-2624.
Bachmann (1987). "Derivations and Genotypes of some Mutant Derivatives of *Escherichia coli* K-I2," Chapter 72 in *Escherichia coli and Salmonella Typhimurium: Cellular and Molecular Biology*, American Society for Microbiology: Washington, DC, 2:1190-1219.
Barbas, C.F. III et al. (Sep. 1991). "Assembly of Combinatorial Antibody Libraries on Phase Surfaces: The Gene III Site," *Proc. Natl. Acad. Sci. USA* 88:7978-7982.

(Continued)

*Primary Examiner* — Nancy J Leith
(74) *Attorney, Agent, or Firm* — Morrison & Foerster LLP

(57) ABSTRACT

The present invention provides methods and compositions for expression and production of recombinant antibodies in a host cell system, such as prokaryotic and eukaryotic expression systems. Particularly contemplated are recombinant systems for temporally separated expression of light chain and heavy chain of antibodies. The antibody products including antibody fragments can be used in various aspects of biological research, diagnosis and medical treatment.

18 Claims, 11 Drawing Sheets

(56) References Cited

U.S. PATENT DOCUMENTS

| | | |
|---|---|---|
| 2005/0005310 A1 | 1/2005 | Chisholm et al. |
| 2005/0170464 A1 | 8/2005 | Simmons et al. |
| 2007/0015244 A1 | 1/2007 | Simmons et al. |
| 2007/0020725 A1 | 1/2007 | Simmons et al. |
| 2007/0065909 A1 | 3/2007 | Simmons et al. |
| 2007/0224664 A1 | 9/2007 | Simmons et al. |

FOREIGN PATENT DOCUMENTS

| | | |
|---|---|---|
| EP | 0 401 384 B1 | 12/1990 |
| EP | 0 404 097 A2 | 12/1990 |
| EP | 0 731 167 A1 | 9/1996 |
| JP | 9-511386 T | 11/1997 |
| JP | 10-508203 T | 8/1998 |
| JP | 2001-500003 T | 1/2001 |
| JP | 2004-530419 T | 10/2004 |
| WO | WO-87/00195 A1 | 1/1987 |
| WO | WO-90/03430 A1 | 4/1990 |
| WO | WO-93/07896 A1 | 4/1993 |
| WO | WO-93/08300 A1 | 4/1993 |
| WO | WO-93/11161 A1 | 6/1993 |
| WO | WO-93/17715 A1 | 9/1993 |
| WO | WO-93/19196 A1 | 9/1993 |
| WO | WO-94/02607 A1 | 2/1994 |
| WO | WO-94/29351 A2 | 12/1994 |
| WO | WO-94/29351 A3 | 12/1994 |
| WO | WO-95/20672 A1 | 8/1995 |
| WO | WO-96/07740 A1 | 3/1996 |
| WO | WO-96/14422 A1 | 5/1996 |
| WO | WO-98/02559 A1 | 1/1998 |
| WO | WO-98/48837 A1 | 11/1998 |
| WO | WO-98/56418 A1 | 12/1998 |
| WO | WO-99/22010 A1 | 5/1999 |
| WO | WO-99/51642 A1 | 10/1999 |
| WO | WO-00/24873 A1 | 5/2000 |
| WO | WO-00/24873 C1 | 5/2000 |
| WO | WO-01/04306 A1 | 1/2001 |
| WO | WO-02/061090 A2 | 8/2002 |
| WO | WO-03/018771 A2 | 3/2003 |
| WO | WO-03/018771 A3 | 3/2003 |

OTHER PUBLICATIONS

Barbas III el al. (Apr. 26, 1994). "In Vitro Evolution of a Neutralizing Human Antibody to Human Immunodeficiency Virus Type 1 to Enhance Affinity and Broaden Strain Cross-Reactivity," *Proc. Natl. Acad. Sci. USA* 91(9):3809-3813.

Bardwell, J.C.A. et al. (Oct. 1994). "Building Bridges: Disulphide Bond Formation in the Cell," *Mol. Micro.* 14(2):199-205.

Barnes et al. (1980). "Methods for Growth of Cultured Cells in Serum-Free Medium," *Analytical Biochemistry* 102:255-270.

Bass et al. (1990). "Hormone Phage: An Enrichment Method for Variant Proteins with Altered Binding Properties," *Proteins: Structure, Function, and Genetics* 8(4):309-314.

Bass, S. et al. (Feb. 1996). "Multicopy Suppressors of prc Mutant *Escherichia coli* Include Two HtrA (DegP) Protease Homologs (HhoAB), DksA, and a Truncated R1pA," *J. Bacteriol.* 178(4):1154-1161.

Battersby, J.E. et al. (Aug. 2001). "Affinity-Reversed-Phase Liquid Chromatography Assay to Quantitate Recombinant Antibodies and Antibody Fragments in Fermentation Broth," *Journal of Chromatography A*, 927(1-2):61-76.

Bibila et al. (1991). "A Structured Model for Monoclonal Antibody Synthesis in Exponentially Growing and Stationary Phase Hybridoma Cells", *Biotechnology and Bioengineering* 37:210-226.

Bird et al. (Oct. 1988). "Single-Chain Antigen-Binding Proteins," *Science* 242:423-426.

Blondel et al. (1991). "Engineering the Quaternary Structure of an Exported Protein with a Leucine Zipper," *Protein Engineering* 4(4):457-461.

Boss et al. (1984). "Assembly of Functional Antibodies from Immunoglobulin Heavy and Light Chains Synthesized in *E. coli*," *Nucleic Acids Res.* 9:3791-3806.

Bothmann et al. (Jun. 2000). "The Periplasmic *Escherichia coli* Peptidylprolyl cis,trans-Isomerase FkpA," *J. Bio. Chem.* 275(22):17100-17105.

Boyd, P.N. et al. (1995). "The Effect of the Removal of Sialic Acid, Galactose and Total Carbohydrate on the Functional Activity of Campath-1H," *Molecular Immunology* 32(17/18):1311-1318.

Brisseau, G.F. et al. (Feb. 15, 1995). "Posttranscriptional Regulation of Macrophage Tissue Factor Expression by Antioxidants," *Blood* 85(4):1025-1035.

Cabilly et al. (1984). "Generation of Antibody Activity from Immunoglobulin Polypeptide Chains Produced in *Escherichia coli,*" *Proc. Natl. Acad. Sci. USA*. 81:3273-3277.

Capel et al. (1994). "Heterogeneity of Human IgG Fc Receptors", *Immunomethods* 4:25-34.

Carter et al. (Feb. 1992). "High Level *Escherichia coli* Expression and Production of a Bivalent Humanized Antibody Fragment", *Bio/Technology* 10(2): 163-167.

Carter el al. (May 1992). "Humanization of an Anti-p185$^{Her2}$ Antibody for Human Cancer Therapy," *Proc. Natl. Acad. Sci.USA* 89:4285-4289.

Casadevall, A. (Jul.-Sep. 1996). "Antibody-Based Therapies for Emerging Infectious Diseases," *Emerging Infectious Diseases* 2(3):200-208.

Chang et al. (1987). "High-level Secretion of Human Growth Hormone by *Escherichia coli*", *Gene* 55: 189-196.

Chari et al. (Jan. 1992). "Immunoconjugates Containing Novel Maytansinoids: Promising Anticancer Drugs", *Cancer Research* 52:127-131.

Chen et al. (Jul. 1999). "Chaperone Activity of DsbC," *J. Bio. Chem.* 274(28): 19601-19605.

Chothia et al. (1987). "Canonical Structures for the Hypervariable Regions of Immunoglobulins," *J. Mol. Biol.* 195:901-917.

Clynes et al. (1998) "Fc Receptors are Required in Passive and Active Immunity to Melanoma," *Proc. Natl. Acad. Sci. USA* 95:652-656.

International Search Report dated Mar. 24, 2004.

Cunningham et al. (1989). "High-Resolution Epitope Mapping of hGH-Receptor Interactions by Alanine-Scanning Mutagenesis," *Science* 244: 1081-1085.

Daëron et al. (1997). "Fc Receptor Biology," *Annu. Rev. Immunol.* 15:203-234.

De Boer et al. (1983). "The tac Promoter: A Functional Hybrid Derived From the trp and lac Promoters," *Proc. Natl. Acad. Sci. USA* 80:22-25.

De Haas et al. (1995). "Fcγ Receptors of Phagocytcs," *J. Lab. Clin. Med.* 126:330-341.

Derrick et al. (Oct. 1992). "Crystal Structure of a Streptococcal Protein G Domain Bound to a Fab Fragment," *Nature* 359:752-754.

Duncan et al. (Apr. 1988). "The Binding Site for C1q on IgG," *Nature* 332(21):738-740.

Edelman, L. et al. (1997). "Obtaining a Functional Recombinant Anti-Rhesus (D) Antibody Using the Baculovirus-Insect Cell Expression System," *Immunology* 91:13-19.

Eigenbrot et al. (1994). "X-Ray Structures of Fragments from Binding and Nonbinding Versions of a Humanized Anti-CD18 Antibody: Structural Indications of the Key Role of $V_H$ Residues 59 to 65," *Proteins: Structure, Function, and Genetics* 18:49-62.

Fendly et al. (Mar. 1, 1990). "Characterization of Murine Monoclonal Antibodies Reactive to Either the Human Epidermal Growth Factor Receptor of HER2/neu Gene Product," *Cancer Research* 50:1550-1558.

Francisco et al. (Jun. 2000). "Agonistic Properties and in Vivo Antitumor Activity of the Anti-CD40 Antibody SGN-14," *Cancer Research* 60:3225-3231.

Friend et al. (1999). "Phase I Study of an Engineered Aglycosylated Humanized CD3 Antibody in Renal Transplant Rejection," *Transplantation* 68:1632-1637.

Guss et al. (1986). "Structure of the IgG-Binding Regions of Streptococcal Protein G," *EMBO Journal* 5:1567-1575.

Guyer et al. (1976). "Immunoglobulin Binding by Mouse Intestinal Epithelial Cell Receptors," *J. Immunol.* 117:587-593.

Ham et al. (1979). "Media and Growth Requirements," *Methods in Enzymology* 58:44-93.

(56) References Cited

OTHER PUBLICATIONS

Hara et al. (1996). "Overproduction of Penicillin-Binding Protein 7 Suppresses Thermosensitive Growth Defect at Low Osmolarity Due to an spr Mutation of *Escherichia coli*," *Micro. Drug Resistance* 2(1):63-72.
Harris (1995). "Therapeutic Monoclonals," *Biochemical Society Transactions* 23:1035-1038.
Hasemann, C.A. et al. (May 1990). "High-level Production of a Functional Immunoglobulin Heterodimer in a Baculovirus Expression System," *Proc. Natl. Acad. Sci. USA* 87:3942-3946.
Hawkins et al. (1992). "Selection of Phage Antibodies by Binding Affinity Mimicking Affinity Maturation," *J. Mol. Biol.* 226:889-896.
Henzel et al. (1994). "Analysis of Two-Dimensional Gel Proteins by Mass Spectrometry and Microsequencing," *Methods: A Companion to Methods Enzymol.* 6:239-247.
Holliger et al. (Jul. 1993). "Diabodies: Small Bivalent and Bispecific Antibody Fragments," *Proc. Natl. Acad. Sci. USA* 90:6444-6448.
Hu et al. (Dec. 1990). "Sequence Requirements for Coiled-Coils: Analysis with a λ Repressor-GCN4 Leucine Zipper Fusions," *Science* 250:1400-1403.
Hurle et al. (1974). "Protein Engineering Techniques for Antibody Humanization," *Curr. Op. Biotech.* 5:428-433.
Huston et al. (Aug. 1988). "Protein Engineering of Antibody Binding Sites: Recovery of Specific Activity in an Anti-Digoxin Single-Chain Fv Analogue Produced in *Escherichia coli*," *Proc. Natl. Acad. Sci. USA* 85:5879-5883.
Idusogie et al. (2000). "Mapping of the C1q Binding Site on Rituxan, a Chimeric Antibody with a Human IgG1 Fc," *J. Immunol.* 164:4178-4184.
International Search Report mailed on Jun. 6, 2003, for International Application No. PCT/US01/48691, filed on Dec. 13, 2001, three pages.
International Search Report mailed on Jun. 16, 2003, for International Application No. PCT/US02/27220, filed on Aug. 26, 2002, two pages.
Isaacs et al. (1996). "A Therapeutic Human IgG4 Monoclonal Antibody that Depletes Target Cells in Humans," *Clin. Exp. Immunol.* 106:427-433.
Jackson et al. (1995). "In Vitro Antibody Maturation," *J. Immunol.* 154(7):3310-3319.
Jones et al. (May 29, 1986). "Replacing the Complementarity-Determining Regions in a Human Antibody with Those From a Mouse," *Nature* 321:522-525.
Kikuchi et al. (1981). "The Nucleotide Sequence of the Promoter and the Amino-Terminal Region of Alkaline Phosphatase Structural Gene (phoA) of *Escherichia coli*," *Nucleic Acids Research* 9(21 ):5671-5678.
Kim et al. (1994). "Localization of the Site of the Murine IgG1 Molecule that is Involved in Binding to the Murine Intestinal Fc Receptor," *J. Imnumol.* 24:2429-2434.
Kipriyanov et al. (1994). "Recombinant Single-Chain Fv Fragments Carrying C-Terminal Cysteine Residues: Production of Bivalent and Biotinylated Miniantibodies," *Molecular Immunology* 31(14):1047-1058.
Kipriyanov et al. (1995). "Single-Chain Antibody Strepavidin Fusions: Tetrameric Bifunctional scFv-Complexes with Biotin Binding Activity and Enhanced Affinity to Antigen," *Human Antibodies and Hybridomas* 6:93-101.
Kipriyanov et al. (1999). "Generation of Recombinant Antibodies," *Mol. Biotech.* 12:173-201.
Kostelny et al. (1992). "Formation of a Bispecific Antibody by the Use of Leucine Zippers," *Journal of Immunology* 148(5):1547-1553.
Lee et al. (Oct. 1983). "Characterization of the Gene Encoding Heat-Stable Toxin II and Preliminary Molecule Epidemiological Studies of Enterotoxigenic *Escherichia coli* Heat-Stable Toxin II Producers," *Infection and Immunity* 42:264-268.

Lindmark et al. (1983). "Binding of Immunoglobulins to Protein A and Immunoglobulin Levels in Mammalian Sera," *J. Immunol. Meth.* 62:1-13.
Liu, W. et al. (Apr. 1998). "Sites Internal to the Coding Regions of *phoA* and *pstS* Bind PhoP and are Required for Full Promoter Activity," *Mol. Microbiol.* 28(1):119-130.
Lo et al. (Jul. 1992). "Expression and Secretion of an Assembled Tetrameric CH2-Deleted Antibody in *E. coli*," *Human Antibodies Hybridomas* 3:123-128.
Marks et al. (1992). "By-Passing Immunization: Building High Affinity Human Antibodies by Chain Shuffling," *Bio/Technology* 10:779-783.
Matsudaira (Jul. 25, 1987). "Sequence from Picomole Quantities of Proteins Electroblotted onto Polyvinylidene Difluoride Membranes," *Journal of Biological Chemistry* 262(21):10035-10038.
Milstein et al. (Oct. 1983). "Hybrid Hybridomas and Their Use in Immunohistochemistry," *Nature* 305:537-540.
Morrison et al. (Nov. 1984). "Chimeric Human Antibody Molecules: Mouse Antigen-Binding Domains with Human Constant Region Domains," *Proc. Natl. Acad. Sci. USA* 81:6851-6855.
Page, M.J. et al. (Jan. 1991). "High Level Expression of the Humanized Monoclonal Antibody Campath-1H in Chinese Hamster Ovary Cells," *Bio/Technology* 9:64-68.
Pallen, M.J. et al. (1997). "The HtrA Family of Serine Proteases," *Mol. Micro.* 26(2):209-221.
Persson, J. et al. (Aug. 5, 2004). "Purification of Antibody and Antibody-Fragment from *E. coli* Homogenate Using 6,9-Diamino-2-ethoxyacridine Lactate as Precipitation Agent," *Biotechnology and Bioengineering* 87(3):424-434.
Picken et al. (1983). "Nuclotide Sequence of the Gene for Heat-Stable Enterotoxin II *Escherichia coli*," *Infection and Immunity* 42(1):269-275.
Plückthun, A. (1994). "*Escherichia coli* Producing Antibodies," Chapter 13 *in Recombinant Microbes for Industrial and Agricultural Applications*, Murooka, Y. et al. eds., Marcel Dekker, Inc.: New York, NY, pp. 233-252.
Pluckthun (1994). "Antibodies From *Escherichia coli*," Chapter II *in The Pharmacology of Monoclonal Antibodies: Handbook of Experimental Pharmacology*, Rosenberg et al. eds., Berlin:Springer-Verlag, vol. 113:269-315.
Pluckthun et al. (1996). "Producing Antibodies in *Escherichia coli*: From PCR to Fermentation," Chapter 10 *in Antibody Engineering: A Practical Approach*, Oxford Press, pp. 203-252.
Pluckthun et al. (Jun. 1997). "New Protein Engineering Approaches to Multivalent and Bispecific Antibody Fragments," *Immunotechnology* 3:83-105.
Posner, B. et al. (1993). "A Revised Strategy for Cloning Antibody Gene Fragments in Bacteria," *Gene* 128:111-117.
Presta et al. (1997). "Humanization of an Anti-Bascular Endothelial Growth Factor Monoclonal Antibody for the Therapy of Solid Tumors and Other Disorders," *Cancer Res.* 57:4593-4599.
Presta et al. (Sep. 1, 1993). "Humanization of an Antibody Directed Against IgE," *J. Immunol.* 151(5):2623-2632.
Presta L. (1992). "Antibody Engineering," *Curr. Op. Struct. Biol.* 2:593-596.
Proba et al. (1995). "Functional Antibody Single-Chain Fragments From the Cytoplasm of *Escherichia coli*: Influence of Thioredoxin Reductase (TrxB)," *Gene* 159:203-207.
Proba et al. (1998). "Antibody scFv Fragments Without Disulfide Bonds Made by Molecular Evolution," *J. Mol. Biol.* 275:245-253.
Ramm et al. (2000). "The Periplasmic *Escherichia coli* Peptidylprolyl cis,trans Isomerase FkpA," *J. Bio. Chem.* 275:17106-17113.
Ravetch et al. (1991). "Fc Receptors," *Annu. Rev. Immunol.* 9:457-492.
Reddy et al. (2000). "Elimination of Fc Receptor-Dependent Effector Functions of a Modified IgG4 Monoclonal Antibody to Human CD4," *J. Immunol.* 164:1925-1933.
Riechmann et al. (Mar 24, 1988). "Reshaping Human Antibodies for Therapy," *Nature* 332:323-327.
Scharff et al. (1970). "Synthesis and Assembly of Immunoglobulin Polypeptide Chains," *Progr. Allergy* 14:37-80.

(56) References Cited

OTHER PUBLICATIONS

Schier et al. (1996). "Identification of Functional and Structural Amino-Acid Residues by Parsimonious Mutagenesis," *Gene* 169:147-155.

Schmiedl, A. et al. (2001). Chapter 18 in *Antibody Engineering*, Springer:Berlin p. 257.

Scholtissek et al. (1987). "A Cloning Cartridge of $\lambda t_o$ Terminator," *Nucl. Acids Res.* 15(7):3185.

Sharma, R.P. et al. (Mar. 1993). "Immunotoxicity of Mycotoxins," *J. Dairy Science* 76(3):892-897.

Siebenlist et al. (1980). "*E. coli* RNA Polymerase Interacts Homologously with Two Different Promoters," *Cell* 20:269-281.

Simmons et al. (May 1996). "Translational Level is a Critical Factor for the Secretion of Heterologous Proteins in *Escherichia coli*," *Nature Biotechnology* 14:629-634.

Simmons, L.C. et al. (May 1, 2002). "Expression of Full-Length Immunglobulins in *Escherichia coli*: Rapid and Efficient Production of Aglocosylated Antibodes," *Journal of Immunological Methods* 262(1-2):133-147.

Sims et al. (Aug. 1993). "A Humanized CD18 Antibody Can Block Function Without Cell Destruction," *The Journal of Immunology* 151(4):2296-2308.

Supplementary European Search Report dated Oct. 12, 2005.

Supplementary European Search Report mailed on Mar. 5, 2008, for EP Application No. 07024871.1, filed on Aug. 26, 2002, three pages.

Sutcliffe (1979). "Complete Nucleotide Sequence of the *Escherichia coli* Plasmid pBR322," *DNA:Replication and Recombination, Cold Spring Harbor Symposia on Quantitative Biology, Cold Spring Harbor Laboratory*, vol. XLIII:77-90.

Thompson et al. (1999). "A Fully Human Antibody Neutralizing Biologically Active Human TGFβ2 for use in Therapy," *J. Immunol Meth.* 227:17-29.

Vaswani, S.K. et al. (Aug. 1998). "Humanized Antibodies as Potential Therapeutic Drugs," *Ann. Allergy, Asthma & Immunol.* 81:105-119.

Verhoeyen et al. (Mar. 25, 1989). "Reshaping Human Antibodies: Grafting an Antilysozyme Activity," *Science* 239:1534-1536.

Verma, R. et al. (1998). "Antibody Engineering: Comparison of Bacterial, Yeast, Insect and Mammalian Expression Systems," *Journal of Immunological Methods* 216: 165-181.

Vitetta, R. et al. (1987). "Redesigning Nature's Poisons to Create Anti-Tumor Reagents," *Science* 238:1098-1104.

Walker, M.R. et al. (1989). "Aglycosylation of Human IgG1 and IgG3 Monoclonal Antibodies can Eliminate Recognition by Human Cells Expressing FcγRI and/or FcγRII Receptors," *Biochem. J.* 259:347-353.

Ward, E.S. et al. (1989). "Binding Activities of a Repertoire of Single Immunoglobulin Variable Domains Secreted from *Escherichia coli*," *Nature* 341:544-546.

Yanofsky et al. (Nov. 1981). "The Complete Nucleotide Sequence of the Tryptophan Operon of *Escherichia coli*," *Nucleic Acids Research* 9(24):6647-6668.

Yansura et al. (1992). "Nucleotide Sequence Selection for Increased Expression of Heterologous Genes in *Escherichia coli*," *Methods: A Companion to Methods in Enzymology* 4(2):151-158.

Yelton et al. (1995). "Affinity Maturation of the BR96 Anti-Carcinoma Antibody by Codon-Based Mutagenesis," *J. Immunol.* 155:1994-2004.

Zapata et al. (1995). "Engineering Linear F(ab')2 Fragments for Efficient Production in *Escherichia coli* and Enhanced Antiproliferative Activity," *Protein Engineering* 8(10):1057-1062.

Zemel-Dreasen et al. (1984). "Secretion and Processing of an Immunoglobulin Light Chain in *Escherichia coli*," *Gene* 27(3):315-322.

Zhu et al. (2000). "The Contribution of Buried Polar Groups to the Conformational Stability of the GCN4 Coiled Coil," *J. Mol. Biol.* 300:1377-1387.

Figure 1: Schematic of the anti-CD18 Fab'2 (-leucine zipper) Plasmids
pS1130
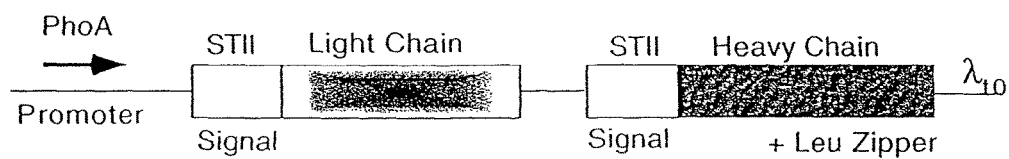
pxCD18-7T3
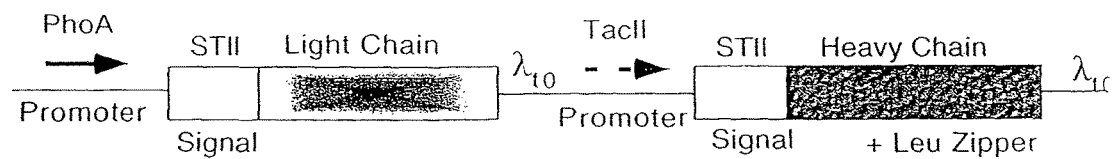

xCD18-7T3.DNA

```
GAATTCAACTTCTCCATACTTTGGATAAGGAAATACAGACATGAAAAATCTCATTGCTGA
GTTGTTATTTAAGCTTGCCCAAAAAGAAGAAGAGTCGAATGAACTGTGTGCGCAGGTAGA
AGCTTTGGAGATTATCGTCACTGCAATGCTTCGCAATATGGCGCAAAATGACCAACAGCG
GTTGATTGATCAGGTAGAGGGGGCGCTGTACGAGGTAAAGCCCGATGCCAGCATTCCTGA
CGACGATACGGAGCTGCTGCGCGATTACGTAAAGAAGTTATTGAAGCATCCTCGTCAGTA
AAAAGTTAATCTTTTCAACAGCTGTCATAAAGTTGTCACGGCCGAGACTTATAGTCGCTT
TGTTTTTATTTTTAATGTATTTGTAACTAGTACGCAAGTTCACGTAAAAAGGGTATCTA
GAATTATGAAAAGAATATCGCATTTCTTCTTGCATCTATGTTCGTTTTTTCTATTGCTA
CAAACGCGTACGCTGATATCCAGATGACCCAGTCCCCGAGCTCCCTGTCCGCCTCTGTGG
GCGATAGGGTCACCATCACCTGTCGTGCCAGTCAGGACATCAACAATTATCTGAACTGGT
ATCAACAGAAACCAGGAAAAGCTCCGAAACTACTGATTTACTATACCTCCACCCTCCACT
CTGGAGTCCCTTCTCGCTTCTCTGGTTCTGGTTCTGGGACGGATTACACTCTGACCATCA
GCAGTCTGCAACCGGAGGACTTCGCAACTTATTACTGTCAGCAAGGTAATACTCTGCCGC
CGACGTTCGGACAGGGCACGAAGGTGGAGATCAAACGAACTGTGGCTGCACCATCTGTCT
TCATCTTCCCGCCATCTGATGAGCAGTTGAAATCTGGAACTGCCTCTGTTGTGTGCCTGC
TGAATAACTTCTATCCCAGAGAGGCCAAAGTACAGTGGAAGGTGGATAACGCCCTCCAAT
CGGGTAACTCCCAGGAGAGTGTCACAGAGCAGGACAGCAAGGACAGCACCTACAGCCTCA
GCAGCACCCTGACGCTGAGCAAAGCAGACTACGAGAAACACAAAGTCTACGCCTGCGAAG
TCACCCATCAGGGCCTGAGCTCGCCCGTCACAAAGAGCTTCAACAGGGGAGAGTGTTAAT
TAAATCCTCTACGCCGGACGCATCGTGGCGAGCTCGGTACCCGGGGATCTAGGCCTAACG
CTCGGTTGCCGCCGGGCGTTTTTTATTGTTGCCGACGCGCATCTCGACTGCACGGTGCAC
CAATGCTTCTGGCGTCAGGCAGCCATCGGAAGCTGTGGTATGGCTGTGCAGGTCGTAAAT
CACTGCATAATTCGTGTCGCTCAAGGCGCACTCCCGTTCTGGATAATGTTTTTTGCGCCG
ACATCATAACGGTTCTGGCAAATATTCTGAAATGAGCTGTTGACAATTAATCATCGAACT
AGTTTAATGTGTGGAATTGTGAGCGGATAACAATTAAGCTTAGGATCTAGAATTATGAAG
AAGAATATTGCGTTCCTACTTGCCTCTATGTTTGTCTTTTCTATAGCTACAAACGCGTAC
GCTGAGGTTCAGCTGGTGGAGTCTGGCGGTGGCCTGGTGCAGCCAGGGGGCTCACTCCGT
TTGTCCTGTGCAACTTCTGGCTACACCTTTACCGAATACACTATGCACTGGATGCGTCAG
GCCCCGGGTAAGGGCCTGGAATGGGTTGCAGGGATTAATCCTAAAAACGGTGGTACCAGC
CACAACCAGAGGTTCATGGACCGTTTCACTATAAGCGTAGATAAATCCACCAGTACAGCC
TACATGCAAATGAACAGCCTGCGTGCTGAGGACACTGCCGTCTATTATTGTGCTAGATGG
CGAGGCCTGAACTACGGCTTTGACGTCCGTTATTTTGACGTCTGGGGTCAAGGAACCCTG
GTCACCGTCTCCTCGGCCTCCACCAAGGGCCCATCGGTCTTCCCCCTGGCACCCTCCTCC
AAGAGCACCTCTGGGGGCACAGCGGCCCTGGGCTGCCTGGTCAAGGACTACTTCCCCGAA
CCGGTGACGGTGTCGTGGAACTCAGGCGCCCTGACCAGCGGCGTGCACACCTTCCCGGCT
GTCCTACAGTCCTCAGGACTCTACTCCCTCAGCAGCGTGGTGACCGTGCCCTCCAGCAGC
TTGGGCACCCAGACCTACATCTGCAACGTGAATCACAAGCCCAGCAACACCAAGGTCGAC
AAGAAAGTTGAGCCCAAATCTTGTGACAAAACTCACACATGCCCGCCGTGCCCAGCACCA
GAACTGCTGGGCGGCCGCATGAAACAGCTAGAGGACAAGGTCGAAGAGCTACTCTCCAAG
AACTACCACCTAGAGAATGAAGTGGCAAGACTCAAAAAGCTTGTCGGGGAGCGCTAAGCA
TGCGACGGCCCTAGAGTCCCTAACGCTCGGTTGCCGCCGGGCGTTTTTTATTGTTAACTC
ATGTTTGACAGCTTATCATCGATAAGCTTTAATGCGGTAGTTTATCACAGTTAAATTGCT
AACGCAGTCAGGCACCGTGTATGAAATCTAACAATGCGCTCATCGTCATCCTCGGCACCG
TCACCCTGGATGCTGTAGGCATAGGCTTGGTTATGCCGGTACTGCCGGGCCTCTTGCGGG
ATATCGTCCATTCCGACAGCATCGCCAGTCACTATGGCGTGCTGCTAGCGCTATATGCGT
```

Figure 2 xCD18-7T3.Protein

STII- xCD18 light chain

MKKNIAFLLASMFVFSIATNAYADIQMTQSPSSLSASVGDRVTITCRASQDINNYLNWY
QQKPGKAPKLLIYYTSTLHSGVPSRFSGSGSGTDYTLTISSLQPEDFATYYCQQGNTLP
PTFGQGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGE
C

STII-xCD18 heavy chain

MKKNIAFLLASMFVFSIATNAYAEVQLVESGGGLVQPGGSLRLSCATSGYTFTEYTMHW
MRQAPGKGLEWVAGINPKNGGTSHNQRFMDRFTISVDKSTSTAYMQMNSLRAEDTAVYY
CARWRGLNYGFDVRYFDVWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKP
SNTKVDKKVEPKSCDKTHTCPPCPAPELLGGRMKQLEDKVEELLSKNYHLENEVARLKK
LVGER

Figure 3

Figure 8: Schematic of the anti-Tissue Factor IgG1 Plasmids
paTF130
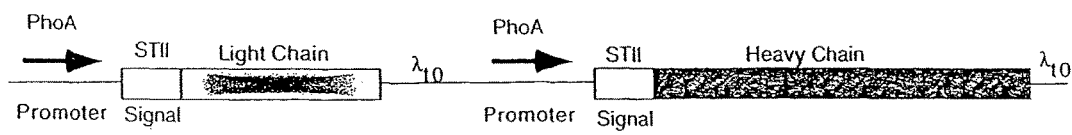
pxTF-7T3FL
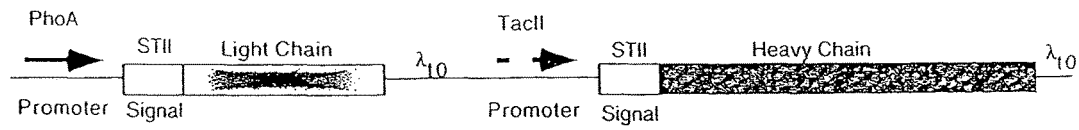

xTF-7T3FL.DNA

```
GAATTCAACTTCTCCATACTTTGGATAAGGAAATACAGACATGAAAAATCTCATTGCTGA
GTTGTTATTTAAGCTTGCCCAAAAAGAAGAAGAGTCGAATGAACTGTGTGCGCAGGTAGA
AGCTTTGGAGATTATCGTCACTGCAATGCTTCGCAATATGGCGCAAAATGACCAACAGCG
GTTGATTGATCAGGTAGAGGGGGCGCTGTACGAGGTAAAGCCCGATGCCAGCATTCCTGA
CGACGATACGGAGCTGCTGCGCGATTACGTAAAGAAGTTATTGAAGCATCCTCGTCAGTA
AAAAGTTAATCTTTTCAACAGCTGTCATAAAGTTGTCACGGCCGAGACTTATAGTCGCTT
TGTTTTTATTTTTTAATGTATTTGTAACTAGTACGCAAGTTCACGTAAAAAGGGTATCTA
GAATTATGAAAAAGAATATCGCATTTCTTCTTGCATCTATGTTCGTTTTTTCTATTGCTA
CAAACGCGTACGCTGATATCCAGATGACCCAGTCCCCGAGCTCCCTGTCCGCCTCTGTGG
GCGATAGGGTCACCATCACCTGCAGAGCCAGTCGCGACATCAAGAGCTATCTGAACTGGT
ATCAACAGAAACCAGGAAAAGCTCCGAAAGTACTGATTTACTATGCTACTAGTCTCGCTG
AAGGAGTCCCTTCTCGCTTCTCTGGATCCGGTTCTGGGACGGATTACACTCTGACCATCA
GCAGTCTGCAGCCAGAAGACTTCGCAACTTATTACTGTCTTCAGCACGGAGAGTCTCCAT
GGACATTTGGACAGGGTACCAAGGTGGAGATCAAACGAACTGTGGCTGCACCATCTGTCT
TCATCTTCCCGCCATCTGATGAGCAGTTGAAATCTGGAACTGCTTCTGTTGTGTGCCTGC
TGAATAACTTCTATCCCAGAGAGGCCAAAGTACAGTGGAAGGTGGATAACGCCCTCCAAT
CGGGTAACTCCCAGGAGAGTGTCACAGAGCAGGACAGCAAGGACAGCACCTACAGCCTCA
GCAGCACCCTGACGCTGAGCAAAGCAGACTACGAGAAACACAAAGTCTACGCCTGCGAAG
TCACCCATCAGGGCCTGAGCTCGCCCGTCACAAAGAGCTTCAACAGGGGAGAGTGTTAAT
TAAATCCTCTACGCCGGACGCATCGTGGCGAGCTCGGTACCCGGGGATCTAGGCCTAACG
CTCGGTTGCCGCCGGGCGTTTTTTATTGTTGCCGACGCGCATCTCGACTGCACGGTGCAC
CAATGCTTCTGGCGTCAGGCAGCCATCGGAAGCTGTGGTATGGCTGTGCAGGTCGTAAAT
CACTGCATAATTCGTGTCGCTCAAGGCGCACTCCCGTTCTGGATAATGTTTTTTGCGCCG
ACATCATAACGGTTCTGGCAAATATTCTGAAATGAGCTGTTGACAATTAATCATCGAACT
AGTTTAATGTGTGGAATTGTGAGCGGATAACAATTAAGCTTAGGATCTAGAATTATGAAG
AAGAATATTGCGTTCCTACTTGCCTCTATGTTTGTCTTTTCTATAGCTACAAACGCGTAC
GCTGAGGTTCAGCTGGTGGAGTCTGGCGGTGGCCTGGTGCAGCCAGGGGGCTCACTCCGT
TTGTCCTGTGCAGGTTCTGGCTTCAATATTAAGGAGTACTACATGCACTGGGTCCGTCAG
GCCCCGGGTAAGGGCCTGGAATGGGTTGGATTGATTGATCCAGAGCAAGGCAACACGATC
TATGACCCGAAGTTCCAGGACCGTGCCACTATAAGCGCTGACAATTCCAAAAACACAGCA
TACCTGCAGATGAACAGCCTGCGTGCTGAGGACACTGCCGTCTATTATTGTGCTCGAGAC
ACGGCCGCTTACTTCGACTACTGGGGTCAAGGAACCCTGGTCACCGTCTCCTCGGCCTCC
ACCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGACTC
TACTCCCTCAGCAGCGTGGTGACTGTGCCCTCTAGCAGCTTGGGCACCCAGACCTACATC
TGCAACGTGAATCACAAGCCCAGCAACACCAAGGTGGACAAGAAAGTTGAGCCCAAATCT
TGTGACAAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTGAGGTC
ACATGCGTGGTGGTGGACGTGAGCCACGAAGACCCTGAGGTCAAGTTCAACTGGTACGTG
GACGGCGTGGAGGTGCATAATGCCAAGACAAAGCCGCGGGAGGAGCAGTACAACAGCACG
TACCGTGTGGTCAGCGTCCTCACCGTCCTGCACCAGGACTGGCTGAATGGCAAGGAGTAC
AAGTGCAAGGTCTCCAACAAAGCCCTCCCAGCCCCCATCGAGAAACCATCTCCAAAGCC
AAAGGGCAGCCCCGAGAACCACAGGTGTACACCCTGCCCCCATCCCGGGAAGAGATGACC
AAGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTACACGCAGAAG
AGCCTCTCCCTGTCTCCGGGTAAATAAGCATGCGACGGCCCTAGAGTCCCTAACGCTCGG
TTGCCGCCGGGCGTTTTTATTGTTAACTCATGTTTGACAGCTTATCATCGATAAGCTTT
AATGCGGTAGTTTATCACAGTTAAATTGCTAACGCAGTCAGGCACCGTGTATGAAATCTA
ACAATGCGCTCATCGTCATCCTCGGCACCGTCACCCTGGA
```

Figure 9 xTF-7T3FL.Protein

STII + Anti-TF light chain

MKKNIAFLLASMFVFSIATNAYADIQMTQSPSSLSASVGDRVTITCRASRDIKSYLNWY
QQKPGKAPKVLIYYATSLAEGVPSRFSGSGSGTDYTLTISSLQPEDFATYYCLQHGESP
WTFGQGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGE
C

STII + Anti-TF heavy chain

MKKNIAFLLASMFVFSIATNAYAEVQLVESGGGLVQPGGSLRLSCAASGFNIKEYYMHW
VRQAPGKGLEWVGLIDPEQGNTIYDPKFQDRATISADNSKNTAYLQMNSLRAEDTAVYY
CARDTAAYFDYWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPGK

Figure 10

SYSTEM FOR ANTIBODY EXPRESSION AND ASSEMBLY

CROSS-REFERENCE TO RELATED APPLICATIONS

This application is a continuation of U.S. patent application Ser. No. 13/033,521, filed Feb. 23, 2011; which is a continuatuion of U.S. patent application Ser. No. 11/438,484, file May 22, 2006; which is a continuation application of U.S. patent application Ser. No. 11/351,886, filed Feb. 9, 2006; which is a continuation of U.S. patent application Ser. No. 10/227,694, filed Aug. 26, 2002; which claims the priority benefit of U.S. Provisional Patent Application No. 60/315,209, filed Aug. 27, 2001, the entire content of each of which is incorporated herein by reference.

FIELD OF THE INVENTION

The present invention relates generally to the fields of molecular biology and protein technology. More specifically, the invention concerns recombinantly produced antibodies and uses thereof.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392004705 SubSeqList.txt, date recorded: Nov. 27, 2013, size: 18 KB).

BACKGROUND OF THE INVENTION

Recent years have seen increasing promises of using antibodies as diagnostic and therapeutic agents for various disorders and diseases. Many research and clinical applications require large quantities of functional antibodies or antibody fragments, thus calling for scaled-up, yet economic systems for antibody production. Particularly useful is the recombinant production of antibodies using a variety of expression hosts, ranging from prokaryotes such as *E. coli* or *B. subtilis*, to yeast, plants, insect cells and mammalian cells. Kipriyanov and Little (1999) *Mol. Biotech.* 12:173-201.

Compared to other antibody production systems, bacteria, particularly *E. coli*, provides many unique advantages. The raw materials used (i.e. bacterial cells) are inexpensive and easy to grow, therefore reducing the cost of products. Prokaryotic hosts grow much faster than, e.g., mammalian cells, allowing quicker analysis of genetic manipulations. Shorter generation time and ease of scaling up also make bacterial fermentation a more attractive means for large quantity protein production. The genomic structure and biological activity of many bacterial species including *E. coli* have been well-studied and a wide range of suitable vectors are available, making expression of a desirable antibody more convenient. Compared with eukaryotes, fewer steps are involved in the production process, including the manipulation of recombinant genes, stable transformation of multiple copies into the host, expression induction and characterization of the products. Pluckthun and Pack (1997) *Immunotech* 3:83-105. In addition, *E. coli* permits a unique access to random approaches. Because of the unparalleled efficiency for transformation by plasmids or transfection by phages, *E. coli* systems can be used for phage library construction of many types of antibody variants, which is particularly important in functional genomic studies.

Various approaches have been used to make recombinant antibodies in bacteria. Like other heterologous proteins, antibody molecules can be obtained from bacteria either through refolding of inclusion bodies expressed in the cytoplasm, or through expression followed by secretion to the bacterial periplasm. The choice between secretion and refolding is generally guided by several considerations. Secretion is usually the faster and more commonly used strategy for producing antibodies. Kipriyanov and Little (1999), supra.

Opper et al., U.S. Pat. No. 6,008,023, describes an *E. coli* cytoplasmic expression system, wherein antibody fragments (e.g., Fabs) are fused with an enzyme for use in targeted tumor therapy. Zemel-Dreasen et al (1984) *Gene* 27:315-322 reports the secretion and processing of an antibody light chain in *E. coli*. Lo et al's PCT publication, WO 93/07896, reports the *E. coli* production of a tetrameric antibody lacking the CH2 region in its heavy chain. The genes encoding the light chain and the CH2-deleted heavy chain were constructed into the same expression vector, under the control of one single promoter.

Antibody expression in prokaryotic systems can be carried out in different scales. The shake-flask cultures (in the 2-5 liter-range) typically generate less than 5 mg/liter products. Carter et al. (1992) *Bio/Technology* 10:12-16 developed a high cell-density fermentation system in which high-level expression (up to 2 g/liter) of antibody fragments was obtained. The gram per liter titers of Fab' obtained by Carter et al. is due largely to higher cell densities resulting from the more precisely controlled environment of a fermentor than that of a simple shake flask. The system contains a dicistronic operon designed to co-express the light chain and heavy chain fragments. The dicistronic operon is under the control of a single *E. coli* phoA promoter which is inducible by phosphate starvation. Each antibody chain is preceded by the *E. coli* heat-stable enterotoxin II (stII) signal sequence to direct secretion to the periplasmic space. The system described by Carter et al. (1992) is further discussed herein below.

For general reviews of antibody production in *E. coli*, see Pluckthun and Pack (1997) *Immunotech* 3:83-105; Pluckthun et al. (1996) in ANTIBODY ENGINEERING: A PRACTICAL APPROACH, pp 203-252 (Oxford Press); Pluckthun (1994) in HANDBOOK OF EXP PHARMCOL VOL 3: THE PHARMCOL OF MONOCLONAL ANTIBODIES, pp 269-315 (ed. M. Rosenberg and G. P. Moore; Springer-Verlag, Berlin).

Many biological assays (such as X-ray crystallography) and clinical applications (such as protein therapy) require large amounts of antibody. Accordingly, a need exists for high yield yet simple systems for producing properly assembled, soluble and functional antibodies.

SUMMARY OF THE INVENTION

The present invention provides novel methods and compositions for recombinantly producing functional antibodies or antibody fragments in host cells, such as prokaryotic or eukaryotic host cells. In one embodiment, the invention provides a process for temporally separating the expression of light chain and heavy chain of an antibody in a host cell such as a prokaryotic cell, thereby increasing the yield of assembled, functional antibody molecules. In particular, the method comprises transforming the host cell with two separate translational units respectively encoding the light and heavy chains; culturing the cell under suitable conditions such that the light chain and heavy chain are expressed in a sequential fashion, thereby temporally separating the production of the light and heavy chains; and allowing the light and heavy chains to assemble into the functional antibody or fragment thereof. In one preferred aspect, the temporally separated expression of light and heavy chains is realized by utilizing two different promoters separately controlling the light and heavy chains, wherein the different promoters are activated under different conditions. For example, DNAs encoding the light and heavy chains can be incorporated into a single plasmid vector but are separated into two translational units, each of which is controlled by a different promoter. One promoter (for example, a first promoter) can be either constitutive or inducible, whereas the other promoter (for example, a second promoter) is inducible. As such, when the host cells transformed with such vector are cultured under conditions suitable for activating one promoter (for example, the first promoter). only one chain (e.g., the light chain) is expressed. Then, after a desirable period of expression of the first chain (e.g. the light chain), culturing conditions are changed to those suitable for the activation of the other promoter (for example, the second promoter), and hence inducing the expression of the second chain (e.g. the heavy chain). In one preferred embodiment, the light chain is expressed first followed by the heavy chain. In another embodiment, the heavy chain is expressed first followed by the light chain.

The invention also provides a recombinant vector for making an assembled functional antibody or fragment thereof in a prokaryotic or eukaryotic host cell, said vector comprising a first promoter preceding a first translational unit encoding a secretion signal operably linked to a light chain; and a second promoter preceding a second translational unit encoding a secretion signal operably linked to a heavy chain. The first and second promoters are inducible under different conditions.

Many prokaryotic and eukaryotic species can be used as hosts for antibody expression according to the invention. Preferably, a prokaryotic host is a gram-negative bacteria. More preferably, the host is *E. coli*. In one aspect, the host cell is a genetically altered *E. coli* strain suitable for large quantity production of heterologous proteins. For example, the host cells may be an *E. coli* strain containing mutant alleles for proteases, and or extra copies of the dsb genes. Many known promoters, constitutive or inducible, are suitable for use in the present invention, so long as they can be used effectively in combination with another promoter.

The methods and compositions of the invention can be used for large quantity production of a wide range of assembled antibody molecules including intact antibody or antibody fragments such as Fab, Fab', F(ab')$_2$, F(ab')$_2$-leucine zipper fusion, Fv and dsFv. Moreover, antibody molecules of the invention can be of human, chimeric, humanized or affinity-matured. The antibody can be specific to any appropriate antigen, preferably those biologically important polypeptides. An antibody fragment may be fused to a dimerization domain, such as a leucine zipper domain.

Also contemplated are various diagnostic and therapeutic uses of the antibodies made according to the methods described herein. In one therapeutic application, the recombinantly made antibody or fragment thereof is used in combination with another therapeutic agent in a treatment.

BRIEF DESCRIPTION OF DRAWINGS

FIG. 1 is a schematic representation of the construction of the antiCD18 F(ab')$_2$(-leucine zipper) plasmids pS1130 (single promoter) and pxCD18-7T3 (dual-promoter).

FIG. 2 depicts the insert nucleic acid sequence of the dual-promoter construct pxCD18-7T3 (SEQ ID NO: 3).

FIG. 3 depicts the amino acid sequences encoded by the two translational units within the construct pxCD18-7T3. N-terminal STII secretion signal sequences are underlined (SEQ ID NOs:1 and 2).

FIG. 8 is a schematic of the anti-Tissue Factor IgG1 plasmids paTF130 (PhoA/PhoA promoters) and pxTF-7T3FL (PhoA/TacII-promoters).

FIG. 9 depicts the insert nucleic acid sequence of the PhoA/TacII-promoter construct pxTF-7T3FL (SEQ ID NO:6).

FIG. 10 depicts the amino acid sequences encoded by the two translational units within the construct pxTF-7T3FL. N-terminal STII secretion signal sequences are underlined (SEQ ID NOs: 4 and 5).

DETAILED DESCRIPTION OF THE PREFERRED EMBODIMENTS

Figure 4:
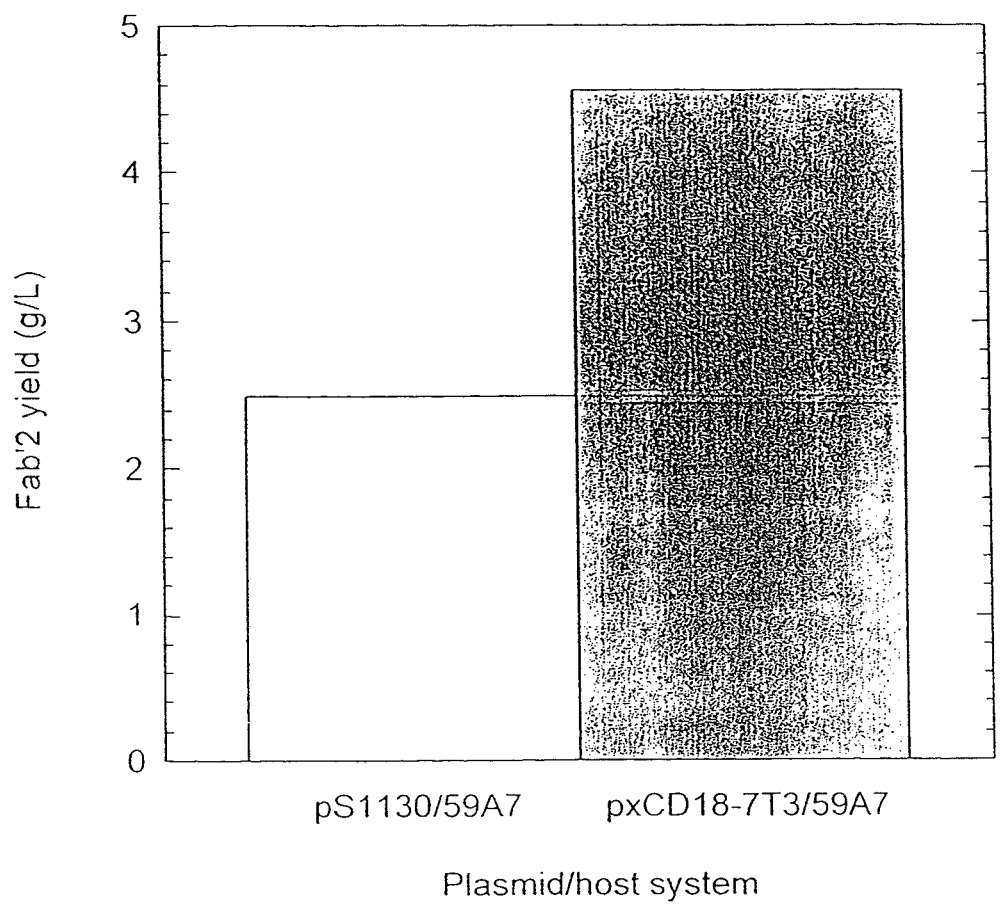
FIG. 4 compares the yields of assembled F(ab')$_2$ using the single promoter system (pS1130/59A7) and the dual promoter system (pxCD18-7T3/59A7).

The principal embodiments of the present invention are based on the surprising discovery that yields of properly assembled, soluble antibodies in a host cell system, such as an *E. coli* fermentation system, can be dramatically increased by temporally separating the induction of the light chain and heavy chain expression. Using a novel recombinant system wherein one chain (e.g., the light chain) was expressed prior to the induction of the second chain (e.g. the heavy chain) expression, about two-fold improvement in titer of assembled antibody has been achieved over a comparable system wherein the light and heavy chains were simultaneously expressed.

Antibodies have traditionally been produced in host cells, such as *E. coli*, using dicistronic vectors, in which genes encoding for light chain and heavy chain are under the control of a single promoter. Under culturing conditions suitable for the activation of the promoter, both light chain and heavy chain genes are expressed simultaneously. For example, Carter et al (1992) *Bio/Technology* 10:163-167 describes a dicistronic operon for light and heavy chain fragments under the control of a single *E. coli* phoA promoter, which is inducible by phosphate starvation. Each antibody chain is preceded by the *E. coli* heat-stable enterotoxin II (stII) signal sequence to direct secretion to the periplasmic space. When this vector was used to carry out certain antibody production, especially when the expression levels of both light chain and heavy chain were high, significant amounts of the individual chain molecules became aggregated, unable to be assembled into soluble and functional antibodies. The problems of aggregation in dicistronic vectors (having a single promoter for both light chain and heavy chain expression) are further illustrated in the Examples provided herein below.

Without being limited to a particular theory, the problem of aggregation could be due, at least partly, to the limited ability of individual chain to fold under the conditions described above. Individual chains of an antibody may behave differently during the process of expression, secretion and assembly into functional antibodies. For example, one chain (e.g. the light chain) may remain predominantly soluble after being secreted alone into the periplasmic space of the host cells, while the other chain (e.g. the heavy chain) would become largely aggregated and insoluble after secretion, unless it exists as part of an assembled antibody complex. Thus, earlier expression of the more soluble chain may facilitate the folding of the less soluble chain and subsequent assembly of the two chains. Additionally, the host cell may have limited capacity for translocating expressed polypeptides via its secretion apparatus. The limit of secretion capacity may be exceeded in certain situations, for example, where multiple polypeptides are expressed simultaneously, or where a great amount, of precursor proteins are expressed by a vector with strong translational strength, or a protein of large size is expressed, or any combination thereof. As the result, less mature proteins are secreted and available for assembly into the antibody complex.

Regardless of the mechanisms, the present invention provides a novel (prokaryotic or eukaryotic) system for antibody production with significantly increased yields of assembled, soluble and functional antibody molecules. Using the dual promoter expression vector of the invention, one chain is synthesized first. After a certain amount of the first chain has been expressed, the expression of the second chain can be induced under a second promoter that is responsive to a changed culturing condition. The newly expressed second chain would then be able to complex with the previously made first chain available to form soluble antibodies or fragments thereof. Thus, by manipulating the timing of the expression of the two chains, more expressed antibody chains could be directed into the soluble antibody complex, increasing the total yield thereof.

While the temporally separate expression system of the present invention is mainly illustrated by the production of antibodies and fragments thereof, it should be understood that the approach described herein is applicable in any system in which multiple protein units/chains are to be produced and an intermediate or final protein complex requires proper assembly of individual units/chains in order to be functional. The approach is especially useful for the production of protein complexes containing immunoglobulin-like domains, such as antibodies, T-cell receptors, class I and class II MHC molecules, integrins, CD8 and CD28 molecules, and related fragments, derivatives, variants and fusion proteins thereof.

Antibody

The term "antibody" is used in the broadest sense and includes monoclonal antibodies, polyclonal antibodies, multivalent antibodies, multispecific antibodies (e.g. bispecific antibodies), and antibody fragments so long as they exhibit the desired biological activity. A naturally occurring antibody comprises four polypeptide chains, two identical heavy (H) chains and two identical light (L) chains inter-connected by disulfide bonds. Each heavy chain is comprised of a heavy chain variable region ($V_H$) and a heavy chain constant region, which in its native form is comprised of three domains, CH1, CH2 and CH3. Each light chain is comprised of a light chain variable region ($V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

The light chains of antibodies from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG-1, IgG-2, IgA-1, IgA-2, and etc. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000).

An antibody may be part of a larger fusion molecule, formed by covalent or noncovalent association of the antibody or antibody portion with one or more other proteins or peptides. Examples of such fusion proteins include use of the streptavidin core region to make a tetrameric scFv molecule (Kipriyanov et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31: 1047-1058).

The present invention encompasses monoclonal antibodies. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

A "functional" or "biologically active" antibody is one capable of exerting one or more of its natural activities in structural, regulatory, biochemical or biophysical events. For example, a functional antibody may have the ability to specifically bind an antigen and the binding may in turn elicit or alter a cellular or molecular event such as signaling transduction or enzymatic activity. A functional antibody may also block ligand activation of a receptor or act as an agonist antibody. The capability of an antibody to exert one or more of its natural activities depends on several factors, including proper folding and assembly of the polypeptide chains. As used herein, the functional antibodies generated by the disclosed methods are typically heterotetramers having two identical L chains and two identical H chains that are linked by multiple disulfide bonds and properly folded.

In some aspects, the present invention encompasses blocking antibodies, antibody antagonists and/or antibody agonists. A "blocking" antibody or an antibody "antagonist" is one which inhibits or reduces biological activity of the antigen it binds. Such blocking can occur by any means, e.g. by interfering with: ligand binding to the receptor, receptor complex formation, tyrosine kinase activity of a tyrosine kinase receptor in a receptor complex and/or phosphorylation of tyrosine kinase residue(s) in or by the receptor. For example. a VEGF antagonist antibody binds VEGF and inhibits the ability of VEGF to induce vascular endothelial cell proliferation. Preferred blocking antibodies or antagonist antibodies completely inhibit the biological activity of the antigen.

An "antibody agonist" is an antibody which binds and activates antigen such as a receptor. Generally, the receptor activation capability of the agonist antibody will be at least qualitatively similar (and may be essentially quantitatively similar) to a native agonist ligand of the receptor.

Antigen Specificity

The present invention is applicable to antibodies or antibody fragments of any appropriate antigen binding specificity. Preferably, the antibodies of the invention are specific to antigens that are biologically important polypeptides. More preferably, the antibodies of the invention are useful for therapy or diagnosis of diseases or disorders in a mammal. The antibodies or antibody fragments obtained according to the present invention are particularly useful as therapeutic agents such as blocking antibodies, antibody agonists or antibody conjugates. Nonlimiting examples of therapeutic antibodies include anti-VEGF, anti-IgE, anti-CD11, anti-CD18, anti-tissue factor, and anti-TrkC antibodies. Antibodies directed against non-polypeptide antigens (such as tumor-associated glycolipid antigens) are also contemplated.

The term "antigen" is well understood in the art and includes substances which are immunogenic, i.e., immunogens, as well as substances which induce immunological unresponsiveness, or anergy, i.e., anergens. Where the antigen is a polypeptide, it may be a transmembrane molecule (e.g. receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD to proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Preferred antigens for antibodies encompassed by the present invention include CD proteins such as CD3, CD4, CD8, CD11a, CD11b, CD18, CD19, CD20, CD34 and CD46; members of the ErbB receptor, family such as the EGF receptor, HER2, HER3 or HER4 receptor; cell adhesion molecules such as LFA-1, Mac1, p150.95, VLA-4, ICAM-1, VCAM, α4/β7 integrin, and αv/β3 integrin including either α or β subunits thereof; growth factors such as VEGF, tissue factor (TF), and TGF-β alpha interferon (α-IFN); an interleukin. such as IL-8; IgE; blood group antigens Apo2, death receptor; flk2/flt3 receptor: obesity (OB) receptor; mpl receptor; CTLA-4; protein C etc. The most preferred targets herein are VEGF, TF, CD19, CD20, CD40, TGF-β, CD11a, CD18, Apo2 and C24.

Soluble antigens or fragments thereof, optionally conjugated to other molecules. can be used as immunogens for generating antibodies. For transmembrane molecules, such as receptors, fragments of these molecules (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

The antibodies of the present invention may be monospecific, bispecific, trispecific or of greater multispecificity. Multispecific antibodies may be specific to different epitopes of a single molecule or may be specific to epitopes on different molecules. Methods for designing and making multispecific antibodies are known in the art. See, e.g., Millstein et al. (1983) *Nature* 305:537-539; Kostelny et al. (1992) *J. Immunol.* 148:1547-1553; WO 93/17715.

Antibody Fragments

The present invention contemplates the prokaryotic or eukaryotic production of antibodies or antibody fragments. Many forms of antibody fragments are known in the art and encompassed herein. "Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., *Nature* 341, 544-546 (1989)) which consists of a VH domain; (vii) isolated CDR regions; (viii) F(ab'), fragments, a bivalent fragment including two Fab' fragments linked by a disulphide bridge at the hinge region; (ix) single chain antibody molecules (e.g. single chain Fv; scFv) (Bird et al., *Science* 242:423-426 (1988); and Huston et al., *PNAS (USA)* 85:5879-5883 (1988)); (x) "diabodies" with two antigen binding sites. comprising a heavy chain variable domain (VH) connected to a light chain variable domain (VL) in the same polypeptide chain (see, e.g., EP 404,097; WO 93/11161; and Hollinger et al., *Proc. Natl. Acad. Sci. USA*, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. *Protein Eng.* 8(10):1057-1062 (1995); and U.S. Pat. No. 5,641,870).

Moreover, the present invention contemplates antibody fragments that are modified to improve their stability and or to create antibody complexes with multivalency. For many medical applications, antibody fragments must be sufficiently stable against denaturation or proteolysis conditions, and the antibody fragments should ideally bind the target antigens with high affinity. A variety of techniques and materials have been developed to provide stabilized and or multivalent antibody fragments. An antibody fragment of the invention may be fused to a dimerization domain. In a preferred embodiment, the antibody fragments of the present invention are dimerized by the attachment of a dimerization domain, such as leucine zippers.

"Leucine zipper" is a protein dimerization motif found in many eukaryotic transcription factors where it serves to bring two DNA-binding domains into appropriate juxtaposition for binding to transcriptional enhancer sequences. Dimerization of leucine zippers occurs via the formation of a short parallel coiled coil, with a pair of α-helices wrapped around each other in a superhelical twist. Zhu et al. (2000) *J. Mol. Biol.* 300:1377-1387. These coiled-coil structures, termed "leucine zippers" because of their preference for leucine in every 7th position, have also been used as dimerization devices in other proteins including antibodies. Hu et al. (1990) Science 250:1400-1403; Blondel and Bedouelle (1991) Protein Eng. 4:457. Several species of leucine zippers have been identified as particularly useful for dimeric and tetrameric antibody constructs. Pluckthun and Pack (1997) *Immunotech.* 3:83-105; Kostelny et al. (1992) *J. Immunol.* 148:1547-1553.

Antibody Variants

Amino acid sequence modification(s) of antibodies or fragments thereof are contemplated. For example, it may be desirable to improve the binding affinity and/or other biological properties of the antibody. Amino acid sequence variants of the antibody are prepared by introducing appropriate nucleotide changes into the antibody nucleic acid. or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) *Science,* 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibodies are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr; cys | cys |

TABLE 1-continued

| Original Residue | Exemplary Substitutions | Preferred Substitutions |
| --- | --- | --- |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability.

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the antibody of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In one embodiment, the Fc region variant may display altered neonatal Fc receptor (FcRn) binding affinity. Such variant Fc regions may comprise an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447 of the Fc region, wherein the numbering of the residues in the Fc region is that of the EU index as in Kabat. Fc region variants with reduced binding to an FcRn may comprise an amino acid modification at any one or more of amino acid positions 252, 253, 254, 255, 288, 309, 386, 388, 400, 415, 433, 435, 436, 439 or 447 of the Fc region, wherein the numbering of the residues in the Fc region is that of the EU index as in Kabat. The above-mentioned Fc region variants may, alternatively, display increased binding to FcRn and comprise an amino acid modification at any one or more of amino acid positions 238, 256, 265, 272, 286, 303, 305, 307, 311, 312, 317, 340, 356, 360, 362, 376, 378, 380, 382, 413, 424 or 434 of the Fc region, wherein the numbering of the residues in the Fc region is that of the EU index as in Kabat.

The Fc region variant with reduced binding to an FcγR may comprise an amino acid modification at any one or more of amino acid positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc region, wherein the numbering of the residues in the Fc region is that of the EU index as in Kabat.

For example, the Fc region variant may display reduced binding to an FcγRI and comprise an amino acid modification at any one or more of amino acid positions 238, 265, 269, 270, 327 or 329 of the Fc region, wherein the numbering of the residues in the Fc region is that of the EU index as in Kabat.

The Fc region variant may display reduced binding to an FcγRII and comprise an amino acid modification at any one or more of amino acid positions 238, 265, 269, 270, 292, 294, 295, 298, 303, 324, 327, 329, 333, 335, 338, 373, 376, 414, 416, 419, 435, 438 or 439 of the Fc region, wherein the numbering of the residues in the Fc region is that of the EU index as in Kabat.

The Fc region variant of interest may display reduced binding to an FcγRIII and comprise an amino acid modification at one or more of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 of the Fc region, wherein the numbering of the residues in the Fc region is that of the EU index as in Kabat.

Fc region variants with altered (i.e. improved or diminished) C1q binding and/or Complement Dependent Cytotoxicity (CDC) are described in WO99/51642. Such variants may comprise an amino acid substitution at one or more of amino acid positions 270, 322, 326, 327, 329, 331, 333 or 334 of the Fc region. See, also, Duncan & Winter *Nature* 322:738-40 (1988); U.S. Pat. Nos. 5,648,260; 5,624,821; and WO94/29351 concerning Fc region variants.

Human, Humanized or Affinity Matured Antibodies

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

The present invention encompasses both human and humanized antibodies. "Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

Various methods for humanizing non-human antibodies are known in the art. For example, humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened to against the entire library of known human variable-domain sequences. The human sequence which is closest to that of the rodent is then accepted as the human framework for the humanized antibody (Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA*, 89:4285; Presta et al. (1993) *J. Immunol.*, 151:2623.

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Antibody Derivatives

The antibodies and antibody variants of the present invention can be further modified to contain additional nonproteinaceous moieties that are known in the art and readily available. Derivatizations are especially useful for improving or restoring biological properties of the antibody or fragments thereof. For example, PEG modification of antibody fragments can alter the stability, in vivo circulating half life, binding affinity, solubility and resistance to proteolysis.

Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and or type of polymers used for derivatization can be determined based on considerations including, but not limited to, the particular properties or functions of the antibody to be improved, whether the antibody derivative will be used in a therapy under defined conditions.

In general, the antibody or antibody fragment produced by a prokaryotic expression system as described herein is aglycosylated and lacks detectable effector activities of the Fc region. In some instances, it may be desirable to at least partially restore one or more effector functions of the native antibody. Accordingly, the present invention contemplates a method for restoring the effector function(s) by attaching suitable moieties to identified residue sites in the Fc region of the aglycosylated antibody. A preferred moiety for this purpose is PEG, although other carbohydrate polymers can also be used. Pegylation may be carried out by any of the pegylation reactions known in the art. See, for example, EP 0401384; EP 0154316; WO 98/48837. In one embodiment, cysteine residues are first substituted for residues at identified positions of the antibody, such as those positions wherein the antibody or antibody variant is normally glycosylated or those positions on the surface of the antibody. Preferably, the cysteine is substituted for residue(s) at one or more positions 297, 298, 299, 264, 265 and 239 (numbering according to the EU index as in Kabat). After expression, the cysteine substituted antibody variant can have various forms of PEG (or pre-synthesized carbohydrate) chemically linked to the free cysteine residues.

Antibody Production
Vector Construction

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operably linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

The term "translational unit," as used herein, is intended to refer to a genetic element comprising the nucleotide sequence coding for a polypeptide chain and adjacent control regions. "Adjacent control regions" include, for example, a translational initiation region (TIR; as defined herein below) and a termination region.

The "translation initiation region" or TIR as used herein refers to a nucleic acid region providing the efficiency of translational initiation of a gene of interest. In general, a TIR within a particular translational unit encompasses the ribosome binding site (RBS) and sequences 5' and 3' to RBS. The RBS is defined to contain, minimally, the Shine-Dalgarno region and the start codon (AUG). Accordingly, a TIR also includes at least a portion of the nucleic acid sequence to be translated. Preferably, a TIR includes the sequence encoding a secretion signal peptide that precedes the sequence encoding for the light or heavy chain within a translational unit. A TIR variant contains sequence variants (particularly substitutions) within the TIR region that alter the efficiency of the TIR, such as its translational strength as defined herein below. Preferably, a TIR variant of the invention contains sequence substitutions within the first 2 to about 14, preferably about 4 to 12, more preferably about 6 codons of the signal sequence that precedes the sequence encoding for the light or heavy chain within a translational unit.

The term "translational strength" as used herein refers to a measurement of a secreted polypeptide in a control system wherein one or more variants of a TIR is used to direct secretion of a polypeptide and the results compared to the wild-type TIR or some other control under the same culture and assay conditions. Without being limited to any one theory, "translational strength" as used herein can include, for example, a measure of mRNA stability, efficiency of ribosome binding to the ribosome binding site, and mode of translocation across a membrane.

"Secretion signal sequence" or "secretion signal peptide" refers to a short amino acid sequence that can be used to direct a newly synthesized protein of interest through a cellular membrane, for example, the inner membrane or both inner and outer membranes of prokaryotes. As such, in prokaryotic cells, for example, the protein of interest such as the light or heavy chain polypeptide is secreted into the periplasm of the prokaryotic host cells or into the culture medium. The secretion signal sequences may be endogenous to the host cells, or they may be exogenous, including signal sequences native to the polypeptide to be expressed. Secretion signal sequences are typically at the N-terminal portion of a polypeptide and are typically removed enzymatically between biosynthesis and secretion of the polypeptide from the cytoplasm. Thus, the secretion signal sequence is usually not present in the final protein product.

The term "host cell" (or "recombinant host cell"), as used herein, is intended to refer to a cell that has been genetically altered, or is capable of being genetically altered by introduction of an exogenous polynucleotide, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

DNA sequences encoding the light and heavy chains of the antibody molecule of the invention can be obtained using standard recombinant DNA techniques. Desired DNA sequences may be isolated and sequenced from antibody producing cells such as hybridoma cells. Alternatively, the DNA can be synthesized using nucleotide synthesizer or PCR techniques. Once obtained, DNAs encoding the light and heavy chains are inserted into a recombinant vector capable of replicating, expressing and secreting heterologous polynucleotides in prokaryotic or eukaryotic hosts. Many vectors that are available and known in the art can be used for the purpose of the present invention. Selection of an appropriate vector will depend mainly on the size of nucleic acids to be inserted and the particular host cell to be transformed with the vector.

In general, recombinant vectors containing replicon and control sequences which are derived from species compatible with the host cell are used as parent vectors for the construction of the specific vectors of the present invention. The vector ordinarily carries as backbone components an origin of replication site as well as marking sequences which are capable of providing phenotypic selection in transformed cells. The origin of replication site is a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria.

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*. One example of a selection scheme utilizes a drug to arrest growth of a host cell. Those cells that are successfully transformed with a heterologous gene produce a protein conferring drug resistance and thus survive the selection regimen. An example of plasmid vector suitable for *E. coli* transformation is pBR322. pBR322 contains genes encoding ampicillin (Amp) and tetracycline (Tet) resistance and thus provides easy means for identifying transformed cells. Derivatives of pBR322 or other microbial plasmids or bacteriophage may also be used as parent vectors. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

According to one embodiment, the recombinant vector of the invention comprises at least two translational units, one for the light chain expression and the other for the heavy chain expression. Moreover, the two translational units for light chain and heavy chain are under the control of different promoters. Promoters are untranslated sequences located upstream (5') to the start of a coding sequence (generally within about 100 to 1000 bp) that control its expression. Such promoters typically fall into two classes, inducible and constitutive. Inducible promoters are promoters that initiate increased levels of transcription from DNA under their control in response to some change in culture conditions, e.g. the presence or absence of a nutrient or a change in temperature or pH.

For the purpose of the present invention, either constitutive or inducible promoters can be used as the first promoter controlling the first chain expression in time, and inducible promoters are used as the second promoter controlling the subsequent second chain expression. In a preferred embodiment, both the first promoter and the second promoter are inducible promoters under tight regulation. A large number of promoters recognized by a variety of potential host cells are well known. The selected promoter sequence can be isolated from the source DNA via restriction enzyme digestion and inserted into the vector of the invention. Alternatively the selected promoter sequences can be synthesized.

Both the native promoter sequence and many heterologous promoters may be used to direct amplification and/or expression of a target gene. However, heterologous promoters are preferred, as they generally permit greater transcription and higher yields of expressed target gene as compared to the native target polypeptide promoter.

Promoters suitable for use with prokaryotic hosts include the PhoA promoter, the β-lactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to translational units encoding the target light and heavy chains using linkers or adaptors to supply any required restriction sites (Siebenlist et al. (1980) Cell 20: 269). More preferred promoters for use in this invention are the PhoA promoter and the TacII promoter. Promoters that are functional in eukaryotic host cells are well known in the art, for example as described in U.S. Pat. No. 6,331,415. Examples of such promoters may include those derived from polyoma, Adenovirus 2 or Simian Virus 40 (SV40).

Each translational unit of the recombinant vector of the invention contains additional untranslated sequences necessary for sufficient expression of the inserted genes. Such essential sequences of recombinant vectors are known in the art and include, for example, the Shine-Dalgarno region located 5'-to the start codon and transcription terminator (e.g., λto) located at the 3'-end of the translational unit.

Each translational unit of the recombinant vector further comprises a signal sequence component that directs secretion of the expressed chain polypeptides across a membrane. In general, the secretion signal sequence may be a component of the vector, or it may be a part of the target polypeptide DNA that is inserted into the vector. The secretion signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, lpp, or heat-stable enterotoxin II (STII) leaders, LamB, PhoE, PelB, OmpA and MBP. In a preferred embodiment of the invention, the signal sequences used in both translational units of the expression system are STII signal sequences or variants thereof. Preferably, the DNA encoding for such signal sequence is ligated in reading frame to the 5'-end of DNA encoding the light or heavy chain, resulting in a fusion polypeptide. Once secreted out of the cytoplasm of the host cell, the signal peptide sequence is enzymatically cleaved off from the mature polypeptide.

In some aspects of the invention, in addition to the timing of the expression, the quantitative ratio of light and heavy chain expression is also modulated in order to maximize the yield of secreted and correctly assembled antibodies or fragments thereof. Such modulation is accomplished by simultaneously modulating translational strengths for light and heavy chains on the recombinant vector of the invention. One technique for modulating translational strength is disclosed in Simmons et al. U.S. Pat. No. 5,840,523. Briefly, the approach utilizes variants of the translational initiation region (TIR) within a translational unit. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleotide sequence (as described below) are preferred. Alterations in the TIR can include, for example, alterations in the number or spacing of Shine-Dalgarno sequences, along with alterations in the signal sequence. One preferred method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

Preferably, a set of vectors is generated with a range of TIR strengths for each translational unit therein. This limited set provides a comparison of expression levels of each chain as well as the yield of antibody products under various TIR strength combinations. TIR strengths can be determined by quantifying the expression level of a reporter gene as described in detail in Simmons et al. U.S. Pat. No. 5,840,523. For the purpose of this invention, the translational strength combination for a particular pair of TIRs within a vector is represented by (N-light, M-heavy), wherein N is the relative TIR strength of light chain and M is the relative TIR strength of heavy chain. For example, (7-light, 3-heavy) means the vector provides a relative TIR strength of about 7 for light chain expression and a relative TIR strength of about 3 for heavy chain expression. Based on the translational strength comparison, the desired individual TIRs are selected to be combined in the expression vector constructs of the invention.

Construction of suitable vectors containing one or more of the above listed components employs standard ligation techniques and or other molecular cloning techniques know in the art. Isolated plasmids or DNA fragments are cleaved, tailored, and re-ligated in the form desired to generate the plasmids required.

For analysis to confirm correct sequences in plasmids constructed, the ligation mixtures are used to transform an *E. coli* strain, and successful transformants are selected by ampicillin or tetracycline resistance where appropriate. Plasmids from the transformants are prepared, analyzed by restriction endonuclease digestion, and/or sequenced by the method of Sanger et al. (1977) *Proc. Natl. Acad. Sci. USA* 74:5463-5467 or Messing et al. (1981) *Nucleic Acids Res.* 9:309, or by the method of Maxam et al. (1980) *Methods in Enzymology* 65:499. A number of automated sequencers commercially available can be used to sequence the plasmids. For example, the ABI PRISM 3700 DNA Analyzer (Applied Biosystems, Foster City, Calif.) is an automated capillary electrophoresis sequencer that analyzes fluorescently labeled DNA fragments. Instructions for the preparation of samples are provided in the Sequencing Chemistry Guide that accompanies the instrument.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. Preferably, gram-negative cells are used. More preferably, *E. coli* cells are used as hosts for the invention.

Many *E. coli* strains are suitable as expression hosts herein or as parent hosts from which modified expression hosts can be created. *E. coli* strains that are known and available in the art include, but not limited to, *E. coli* W3110 (ATCC 27,325), *E. coli* 294 (ATCC 31,446), *E. coli* B, *E. coli* 1776 (ATCC 31,537) and *E. coli* RV308(ATCC 31,608). Mutant cells of any of the above-mentioned bacteria may also be employed. It is, of course, necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC177, or pKN410 are used to supply the replicon. Preferably the host cell should secrete minimal amounts of proteolytic enzymes, and additional protease inhibitors may desirably be incorporated in the cell culture.

Suitable eukaryotic host cells are also known in the art. For example, host cells may include yeast, VERO, HeLa, CHO, W138, BHK, COS-7 and MDCK cells.

Transformation and Growth of the Host Cells

Host cells are transformed or transfected (the terms "transformed" and "transfected" are used interchangeably herein) with the above-described recombinant vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation. Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Prokaryotic cells used to produce the polypeptides of the invention are grown in media known in the art and suitable for culture of the selected host cells. Examples of suitable media include luria broth (LB) plus necessary nutrient supplements. In preferred embodiments, the media also contains a selection agent, chosen based on the construction of the expression vector, to selectively permit growth of prokaryotic cells containing the expression vector. For example, ampicillin is added to media for growth of cells expressing ampicillin resistant gene. Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

Eukaryotic host cells used to produce antibodies of the invention can be cultured in a variety of media known in the art. For example, commercially available media such as Ham's F10 (Sigma), Minimal Essential Medium ((MEM), Sigma), RPMI-1640 (Signma), and Dulbecco's Modified Eagle's Medium ((DMEM), Sigma) are suitable for culturing mammalian eukaryotic host cells. In addition, any of the media described in Ham and Wallace, *Meth. Enz.*, 58: 44 (1979), Barnes and Sato, *Anal. Biochem.*, 102:255 (1980), U.S. Pat Nos. 4,767,704; 4,657,866; 4,927,762; or 4,560,655; WO 90/03430; WO 87/00195; U.S. Pat. Re. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Temporally Separate Expression of Light and Heavy Chains

Once the host cells are grown to a certain density, the culturing conditions are modified to promote the synthesis of the protein(s). According to the present invention, the light and heavy chains are induced at different time during the synthesis phase. In one aspect, the temporally separate expression of light and heavy chains is realized by using a dual-promoter vector as described above. If inducible promoter(s) are used in the dual-promoter vector of the invention, protein expression is induced under conditions suitable for the activation of the promoter. In a preferred embodiment, both promoters are inducible. More preferably, the dual promoters are phoA and TacII, respectively. For example, a vector can be made wherein a phoA promoter is used for controlling transcription of the light chain, and a TacII promoter is used for controlling transcription of the heavy chain. During the first stage of induction, prokaryotic host cells transformed with such a phoA/TacII dual promoter vector are cultured in a phosphate-limiting medium for the induction of the phoA promoter and the expression of the light chain. After a desired period of time for light chain expression, sufficient amount of IPTG is added to the culture for the induction of the TacII promoter and the production of the heavy chain.

In one aspect, the antibody or antibody fragment of the invention can be expressed in the cytoplasm of a host bacteria cells. Various methods can be used to improve production of soluble and functional antibodies or antibody fragments in *E. coli* cytoplasm. For example, *E. coli* strains deficient in the trxB gene have been found to enhance the formation of disulfide bonds in the cytoplasm and therefore useful for promoting expression of functional antibody molecules with proper disulfide bond formations in the cytoplasm. Proba et al. (1995) *Gene* 159:203-207. Antibody fragment variants can be made to replace cysteine residues such that the variant does not require formation of disulfide bonds in both $V_H$ and $V_L$, such antibody fragment variants, sometime referred to as "intrabodies", can therefore be made in a reducing environment that is not compatible with efficient disulfide bridge formation, such as in bacteria cytoplasm. Proba et al. (1998) *J. Mol. Biol.* 275:245-253.

When secretion signal sequences are used in the vector of the invention, the expressed light and heavy chain polypeptides are secreted into, and recovered from, the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, the antibody is produced in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers or other suitable means to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-270. A variety of inducers may be used, according to the vector construct employed, as is known in the art and described above. Cells may be grown for shorter periods prior to induction. Cells are usually induced for about 12-50 hours, although longer or shorter induction time may be used.

To further improve the production yield and quality of the antibody molecules of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun (2000) *J. Biol. Chem.* 275:171.06-17113; Arie et al. (2001) *Mol. Microbiol.* 39:199-210. Sufficient disulfide bonds are particularly important for the formation and folding of full length, bivalent antibodies having two heavy chains and two light chains.

To minimize proteolysis of expressed heterologous proteins (especially those that are proteolytically sensitive) such as in prokaryotic host cells, certain host strains deficient for proteolytic enzymes can be used for the present invention.

For example, prokaryotic host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al. (1996) *Microbial Drug Resistance* 2:63-72.

Antibody Purification

Antibody compositions prepared from the host cells are preferably subjected to at least one purification step. Examples of suitable purification steps include hydroxylapatite chromatography, gel electrophoresis, dialysis, and affinity chromatography, with affinity chromatography being the preferred purification technique. The suitability of particular protein as an affinity ligand depends on the species and isotype of any immunoglobulin Fc domain that is present in the antibody. For example, protein A can be used to purify antibodies that are based on human γ1, γ2, or γ4 heavy chains. Lindmark et al. (1983) *J. Immunol. Meth.* 62:1-13. Protein G is recommended for all mouse isotypes and for human γ3 Guss et al. (1986) *EMBO J.* 5:15671575. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

In a preferred embodiment, the antibody produced herein is further purified to obtain preparations that are more substantially homogeneous for further assays and uses. For example, the hydrophobic interaction chromatography (HIC), particularly the low pH HIC (LPHIC) as described in the U.S. Pat. No. 5,641,870, can be used for further purification. In particular, LPHIC provides a way to remove a correctly folded and disulfide bonded antibody from unwanted contaminants (e.g., incorrectly associated light and heavy fragments).

Activity Assays

The antibody of the present invention can be characterized for its physical/chemical properties and biological functions by various assays known in the art. In one aspect of the invention, it is important to compare the antibody made in the dual-promoter systems of the present invention to similar antibodies made in other expression systems, such as different expression vector designs or different host cell systems. Particularly, the quantity of the assembled antibody complex expressed by the dual-promoter vector of the present invention can be compared to those expressed by various polycistronic vectors. Methods for protein quantification are well known in the art. For example, samples of the expressed proteins can be compared for their quantitative intensities on a Coomassie-stained SDS-PAGE. Alternatively, the specific band(s) of interest (e.g., the assembled band) can be detected by, for example, western blot gel analysis.

The purified antibody can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the antibody produced herein is analyzed for its biological activity. Preferably, the antibody of the present invention is tested for its antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. An example of an antigen binding assay is provided below in the Examples section.

Uses of the Antibody

An antibody of the present invention may be used, for example, to purify, detect, and target a specific polypeptide it recognizes, including both in vitro and in vivo diagnostic, prophylactic or therapeutic methods for a variety of disorders or diseases.

A "disorder" is any condition that would benefit from treatment with the antibody. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

An "autoimmune disease" herein is a non-malignant disease or disorder arising from and directed against an individual's own tissues. The autoimmune diseases herein specifically exclude malignant or cancerous diseases or conditions, especially excluding B cell lymphoma, acute lymphoblastic leukemia (ALL), chronic lymphocytic leukemia (CLL), Hairy cell leukemia and chronic myeloblastic leukemia. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitis); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; antiglomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiffman syndrome; Behcet disease; giant cell arteritis; immune complex nephritis; IgA nephropathy; IgM polyneuropathies; immune thrombocytopenic purpura (ITP) or autoimmune thrombocytopenia etc.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

An "effective amount" refers to an amount effective, at dosages and for periods of to time necessary, to achieve the desired therapeutic or prophylactic result. A "therapeutically effective amount" of the antibody may vary according to factors such as the disease state, age, sex, and weight of the individual, and the ability of the antibody to elicit a desired response in the individual. A therapeutically effective amount is also one in which any toxic or detrimental effects of the antibody are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

In one aspect, an antibody of the invention can be used in immunoassays for qualitatively and quantitatively measuring specific antigens in biological samples. Conventional methods for detecting antigen-antibody binding includes, for example, an enzyme linked immunosorbent assay (ELISA), an radioimmunoassay (RIA) or tissue immunohistochemistry. Many methods may use a label bound to the antibody for detection purposes. The label used with the antibody is any detectable functionality that does not interfere with its binding to antibody. Numerous labels are known, including the radioisotopes $^{32}P$, $^{32}S$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, .beta.-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, lactoperoxidase, biotin/avidin, spin labels, bacteriophage labels, stable free radicals, imaging radionuclides (such as Technecium) and the like.

Conventional methods are available to bind these labels covalently to the antibody polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al. *Nature* 144: 945 (1962); David et al. *Biochemistry* 13:1014-1021 (1974); Pain et to al. *J. Immunol. Methods* 40:219-230 (1981); and Nygren *Histochem. and Cytochem* 30:407-412 (1982). Preferred labels herein are enzymes such as horseradish peroxidase and alkaline phosphatase. The conjugation of such label, including the enzymes, to the antibody-polypeptide is a standard manipulative procedure for one of ordinary skill in immunoassay techniques. See, for example, O'Sullivan et al., "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166. Such bonding methods are suitable for use with the antibody polypeptides of this invention.

Alternative to labeling the antibody, antigen can be assayed in biological fluids by a competition immunoassay utilizing a competing antigen standard labeled with a detectable substance and an unlabeled antibody. In this assay, the biological sample, the labeled antigen standards and the antibody are combined and the amount of labeled antigen standard bound to the unlabeled antibody is determined. The amount of tested antigen in the biological sample is inversely proportional to the amount of labeled antigen standard bound to the antibody.

In one aspect, the antibody of the invention is particularly useful to detect and profile expressions of specific surface antigens in vitro or in vivo. The surface antigen can be specific to a particular cell or tissue type, therefore serving as a marker of the cell or tissue type. Preferably, the surface antigen marker is differentially expressed at various differentiation stages of particular cell or tissue types. The antibody directed against such surface antigen can thus be used for the screening of cell or tissue populations expressing the marker. For example, the antibody of the invention can be used for the screening and isolation of stem cells such as embryonic stem cells, hematopoietic stem cells and mesenchymal stem cells. The antibody of the invention can also be used to detect tumor cells expressing tumor-associated surface antigens such HER2, HER3 or HER4 receptors.

The antibody of the invention may be used as an affinity purification agent. In this process, the antibody is immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized antibody. Finally, the support is washed with another suitable solvent, such as glycine buffer, pH 5.0, that will release the antigen from the antibody.

The antibody of the invention can be used as an antagonist to partially or fully block the specific antigen activity both in vitro and in vivo. Moreover, at least some of the antibodies of the invention can neutralize antigen activity from other species. Accordingly, the antibodies of the invention can be used to inhibit a specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse).

In another embodiment, an antibody of the invention can be used in a method for inhibiting an antigen in a subject suffering from a disorder in which the antigen activity is detrimental, comprising administering to the subject an antibody of the invention such that the antigen activity in the subject is inhibited. Preferably, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration). Blocking antibodies of the invention that are therapeutically useful include, for example but not limited to, anti-VEGF, anti-IgE, anti-CD11 and anti-tissue factor antibodies. The blocking antibodies of the invention can be used to diagnose, treat, inhibit or prevent diseases, disorders or conditions associated with abnormal expression and or activity of one or more antigen molecules, including but not limited to malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

In one aspect, the blocking antibody of the invention is specific to a ligand antigen, and inhibits the antigen activity by blocking or interfering with the ligand-receptor interaction involving the ligand antigen, thereby inhibiting the corresponding signal pathway and other molecular or cellular events. The invention also features receptor-specific antibodies which do not necessarily prevent ligand binding but interfere with receptor activation, thereby inhibiting any responses that would normally be initiated by the ligand binding. The invention also encompasses antibodies that either preferably or exclusively bind to ligand-receptor complexes. The antibody of the invention can also act as an agonist of a particular antigen receptor, thereby potentiating, enhancing or activating either all or partial activities of the ligand-mediated receptor activation.

In certain embodiments, an immunoconjugate comprising the antibody conjugated with a cytotoxic agent is made and used. Preferably, the immunoconjugate and/or antigen to which it is bound is/are internalized by the cell, resulting in increased therapeutic efficacy of the immunoconjugate in killing the target cell to which it binds. In a preferred embodiment, the cytotoxic agent targets or interferes with nucleic acid in the target cell.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, Ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin $\gamma_1^1$ and calicheamicin $\theta^1_1$, see, e.g., Agnew Chem. Intl. Ed. Engl. 33:183-186 (1994); dynemicin, including dynemicin A; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Conjugates of an antibody and one or more small molecule toxins, such as a calicheamicin, a maytansine (U.S. Pat. No. 5,208,020), a trichothene, and CC1065 are also contemplated herein.

In one preferred embodiment of the invention, the antibody is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al. *Cancer Research* 52: 127-131 (1992)) to generate a maytansinoid-antibody immunoconjugate.

Another immunoconjugate of interest comprises an antibody conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^1$, $\alpha_2^1$, $\alpha_3^1$, N-acetyl-$\gamma_1^1$, PSAG and $\theta^1_1$ (Hinman et al. *Cancer Research* 53: 3336-3342 (1993) and Lode et al. *Cancer Research* 58: 2925-2928 (1998)). See, also, U.S. Pat. Nos. 5,714,586; 5,712,374; 5,264,586; and 5,773,001.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g. a ribonuclease or a DNA endonuclease such as a deoxyribonuclease; DNase).

A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127-131 (1992)) may be used.

Alternatively, a fusion protein comprising the antibody and cytotoxic agent may be made, e.g. by recombinant techniques or peptide synthesis.

In yet another embodiment, the antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

Antibodies of the present invention can be used either alone or in combination with other compositions in a therapy. For instance, the antibody may be co-administered with another antibody, chemotherapeutic agent(s) (including cocktails of chemotherapeutic agents), other cytotoxic agent(s), anti-angiogenic agent(s), cytokines, and/or growth inhibitory agent(s). Where the antibody inhibits tumor growth, it may be particularly desirable to combine the antibody with one or more other therapeutic agent(s) which also inhibits tumor growth. For instance, anti-VEGF antibodies blocking VEGF activities may be combined with anti-ErbB antibodies (e.g. HERCEPTIN® anti-HER2 antibody) in a treatment of metastatic breast cancer. Alternatively, or additionally, the patient may receive combined radiation therapy (e.g. external beam irradiation or therapy with a radioactive labelled agent, such as an antibody). Such combined therapies noted above include combined administration (where the two or more agents are included in the same or separate formulations), and separate administration, in which case, administration of the antibody can occur prior to, and/or following, administration of the adjunct therapy or therapies.

The antibody (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Preferably the dosing is given by injections, most preferably intravenous or subcutaneous injections, depending in part on whether the administration is brief or chronic.

The antibody composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as used hereinbefore or about from 1 to 99% of the heretofore employed dosages.

For the prevention or treatment of disease, the appropriate dosage of the antibody (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The preferred dosage of the antibody will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Pharmaceutical Formulations

Therapeutic formulations of the antibody are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, macroemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Articles of Manufacture

In another embodiment of the invention, an article of manufacture containing materials useful for the treatment of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice, such as cancer. Moreover, the article of manufacture may comprise (a) a first container with a composition contained therein, wherein the composition comprises a antibody; and (b) a second container with a composition contained therein, wherein the composition comprises a further cytotoxic agent. The article of manufacture in this embodiment of the invention may further comprise a package insert indicating that the first and second antibody compositions can be used to treat cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples are intended merely to illustrate the practice of the present invention and are not provided by way of limitation. The disclosures of all patent and scientific literatures cited herein are expressly incorporated in their entirety by reference.

EXAMPLES

Example 1

Production of antiCD18 Antibody Fragments

Materials & Methods
Plasmid Construction

The control plasmid, pS1130, was designed for the dicistronic expression of anti-CD18 F(ab')$_2$ and it was based on the vector described by Carter et al. (1992) *Bio/Technology* 10:163-167. This design places transcription of the genes for both light chain and the heavy chain fragment with a C-terminal leucine zipper under the control of a single phoA promoter. Transcription ends with a $\lambda t_0$ transcriptional terminator located downstream of the coding to sequence for the heavy chain-leucine zipper (Scholtissek and Grosse (1987) *Nucleic Acids Res.* 15(7): 3185). The heat stable enterotoxin II signal sequence (STII) precedes the coding sequence for each chain and directs the secretion of the polypeptide into the periplasm (Lee et al. (1983) *Infect. Immun.* 42: 264-268; Picken et al. (1983) *Infect. Immun.* 42: 269-275). Leucine zipper was attached to the C-terminal end of heavy chain fragment to promote the dimerization of the two Fab' arms.

The dual-promoter plasmid containing two separate translational units, pxCD18-7T3, temporally separates the transcription of light chain from the transcription of heavy chain. As in pS1130, light chain remains under the control of the phoA promoter. However, in pxCD18-7T3, a $\lambda t_0$ transcriptional terminator follows the light chain coding sequence. Downstream of this terminator, the TacII promoter was added to control the transcription of the heavy chain fragment/C-terminal leucine zipper (DeBoer, et al. (1983) *Proc. Natl. Acad. Sci. USA* 80:21-25). A second $\lambda t_0$ transcriptional terminator follows this coding sequence. Silent codon variants of the STII signal sequence were used to direct the secretion of both chains (Simmons and Yansura (1996) *Nature Biotechnology* 14:629-634).

A schematic comparison of the single promoter control plasmid vs. the dual-promoter plasmid is depicted in FIG. 1. The expression cassette sequence of pxCD18-7T3 is provided in FIG. 2 (SEQ ID NO:3) and the amino acid sequences from the two translational units are shown in FIG. 3 (SEQ ID NOs:1 and 2).

Fermentation

The host strain used in fermentation was a derivative of *E. coli* W3110, designated 59A7. The complete genotype of 59A7 is W3110 ΔfhuA phoAΔE15 Δ(argF-lac)169 deoC2 degP41(ΔpstI-Kan$^r$) IN(rrnD-rrnE) 1 ilvG2096(Val$^r$) Δprc prc-suppressor. The 59A7 host cells were transformed with either pS1130 or pxCD18-7T3 plasmid and successful transformants were selected and grown in culture. In the case of the dual-promoter plasmid, an additional plasmid, pMS421, was co-transformed along with pxCD18-7T3. This additional plasmid, pMS421, is a pSC101-based plasmid which provides lacIq to improve control of the TacII promoter, and which also confers spectinomycin and streptomycin resistance.

For each 10-liter fermentation, a single vial containing 1.5 ml of culture in 10-15% DMSO was thawed into a 1 L shake flask containing 500 ml of LB medium supplemented with 0.5 ml of tetracycline solution (5 mg/ml) and 2.5 ml 1M sodium phosphate solution. This seed culture was grown for approximately 16 hours at 30° C. and was then used to inoculate a 10-liter fermentor.

The fermentor initially started with approximately 6.5 liters of medium containing about 4.4 g of glucose, 100 ml of 1 M magnesium sulfate, 10 ml of a trace element solution (100 ml hydrochloric acid, 27 g ferric chloride hexahydrate, 8 g zinc sulfate heptahydrate, 7 g cobalt chloride hexahydrate, 7 g sodium molybdate dihydrate, 8 g cupric sulfate pentahydrate, 2 g boric acid, 5 g manganese sulfate monohydrate, in a final volume of 1 liter), 20 ml of a tetracycline solution (5 mg/ml in ethanol), 10 ml of Fermax Adjuvant 27 (or some equivalent anti-foam), 1 bag of HCD salts (37.5 g ammonium sulfate, 19.5 g potassium phosphate dibasic, 9.75 g sodium phosphate monobasic dihydrate, 7.5 g sodium citrate dihydrate, 11.3 g potassium phosphate monobasic), and 200 g of NZ Amine A (a protein hydrolysate). Fermentations were performed at 30° C. with 10 slpm of air flow and were controlled at a pH of 7.0±0.2 (although occasional excursions beyond this range occurred in some cases). The back pressure of the fermentor and agitation rate were varied to manipulate the oxygen transfer rate in the fermentor, and consequently, control the cellular respiration rate.

Following inoculation of the fermentor with the cell-containing medium from the shake flask, the culture was grown in the fermentor to high cell densities using a computer-based algorithm to feed a concentrated glucose solution to the fermentor. Ammonium hydroxide (58% solution) and sulfuric acid (24% solution) were also fed to the fermentor as needed to control pH. Further additions of anti-foam were also used in some cases to control foaming. When the culture reached a cell density of approximately 40 OD550, an additional 100 ml of 1M magnesium sulfate was added to the fermentor. Additionally, a concentrated salt feed (consisting of approximately 10 g ammonium sulfate, 26 g dibasic potassium phosphate, 13 g monobasic sodium phosphate dihydrate, 2 g sodium citrate dihydrate and 15 g monobasic potassium phosphate in 1L of water) to the fermentor was started at a rate of 2.5 ml/min when the culture reached approximately 20 OD550 and continued until approximately 1250 ml were added to the fermentation. Fermentations were typically continued for 72-80 hours.

During the fermentation, once the dissolved oxygen setpoint for the fermentation was reached, the concentrated glucose solution was fed based on the dissolved oxygen probe signal in order to control the dissolved oxygen concentration at the setpoint. Consequently, in this control scheme, manipulations of fermentor operating parameters such as the agitation rate or back pressure, which affect the oxygen transfer capacity in the fermentation, correspondingly manipulated the oxygen uptake rate or metabolic rate of the cells.

A mass spectrometer was used to monitor the composition of the off-gas from the fermentations and enabled the calculation of the oxygen uptake and carbon dioxide evolution rates in the fermentations.

When the culture reached a cell density of approximately 220 OD550, the agitation was decreased from an initial rate of 1000 rpm to approximately 725 rpm over approximately 12 hours. For the fermentation of the pxCD18-7T3 system (wherein the TacII promoter was used to control heavy chain expression), 50 ml of 200 mM IPTG was added to induce heavy chain synthesis approximately 12 hours after the culture reached a cell density of 220 OD550.

Product Assays

To assess the quantity of the antibody fragments produced in the fermentations, a number of protein assays were used. To determine the quantity of the assembled anti-CD18 F(ab')$_2$-leucine zipper complex, a protein G assay was used. Derrich and Wigley (1992) Nature 359:752-4. To prepare samples for this assay, whole fermentation broth was first sonicated and diluted 2.4× with 50 mM magnesium sulfate. Polyethyleneimine (PEI) was added to a final concentration of 0.1%. After a 20 minute incubation, the samples were centrifuged for approximately 20 minutes at approximately 14,000×g in a microfuge. The supernatant was then diluted 2× with phosphate buffered saline and loaded on a protein G column (Poros G/M column) using a HP 1090 or HP 1100 HPLC system. A 7 minute assay was used in which the column was first equilibrated with 10 mM PO4/300 mM NaCl (pH 8). Following injection of the sample, the column was rinsed with the equilibration buffer for approximately 5.5 minutes (using approx. 3 ml of buffer in a 2.1×30 mm column), followed by a step elution using 30 mM PO4/150 mM NaCl/0.01% TFA (pH 1.9).

To confirm that the protein G results indeed represented assembled F(ab')$_2$ complex, product was also purified through multiple chromatography steps including ion exchange and, after removal of the leucine zipper portion using immobilized pepsin, an additional, ion exchange column and a phenyl sepharose HIC column. Purified product was characterized by a number of routine methods, such as a cation exchange assay, a capillary zone electrophoresis non-gel sieving assay, and SDS-PAGE gels.

To assess the total quantity of light chain and heavy chain fragments produced in the fermentations, an alternative reversed-phase HPLC assay was used. Samples used for this assay were prepared as described above for the protein G assay. The soluble lysate samples were diluted in 6M Guanidine-HCl, 50 mM TRIS, pH 9 (typically 100 µl of sample was diluted with 650 µl of the guanidine solution). 50 µl of 2M dithiothreitol (freshly thawed) was then added. Prior to loading on the HPLC, 200 µl of acetonitrile was added and filtered through a 0.2 µm filter.

For the reversed-phase methodology, a Hewlett-Packard™ 1100 HPLC was used with a Perseptive Poros™ R-1 reversed phase column. Analyses were run with the column heated to 60-80° C. and UV absorbance at 278 nm was monitored. The column was equilibrated in a 28% acetonitrile solution in water with 0.1% trifluoroacetic acid. 25 µl of sample was next loaded on the column, and elution was performed using a linear gradient from 28% to 38% acetonitrile over 20 minutes followed by a 17 minute period of regeneration at 95% acetonitrile and re-equilibration at 28% acetonitrile. Peaks for light chain and heavy chain-related species were identified by comparison with standards and analysis using mass spectrometry for confirmation. Fermentation samples from a blank run in which the same host was used except with a plasmid not containing the sequences for heavy and light chain, were similarly prepared and analyzed to determine the appropriate baselines for the analyses. Integration of the peak areas was performed using the Hewlett-Packard™ 1100 software and standards were spiked into blank run samples to generate a calibration curve in order to quantify the relative quantity of the various species in the samples.

The insoluble lysate samples were also similarly analyzed by resuspending the insoluble pellets obtained from cell lysates in 950 µl of 6M Guanidine/HCl, 50 mM TRIS, pH 9+50 µl 2M dithiothreitol. Sonication (5 to 10 pulses) was typically performed to aid in to resolubilizing the pellets followed by the dilution of 100 µl of the resuspended pellet in 650 µl of the guanidine solution+50 µl 2M dithiothreitol+ 200 mM acetonitrile. The samples were then filtered and analyzed using the same method as for the soluble lysate samples.

Results

A series of anti-CD18 F(ab')$_2$ fermentation runs were conducted using either the pS1130 single promoter system or the pxCD18-7T3 dual-promoter system. The yields of assembled anti-CD18 F(ab')$_2$ complex were measured and calculated using the protein assays described in the Methods and Materials section. As shown in FIG. 4, which is a bar graph representing the fermentation yields (g/L), use of the phoA-tac dual-promoter vector in the strain 59A7 increased yields of assembled F(ab')$_2$ from approximately 2.5 g/L for the best pS1130/59A7 transformant identified to approximately 4.6±0.5 g/L, a nearly two-fold increase.

Figure 5:
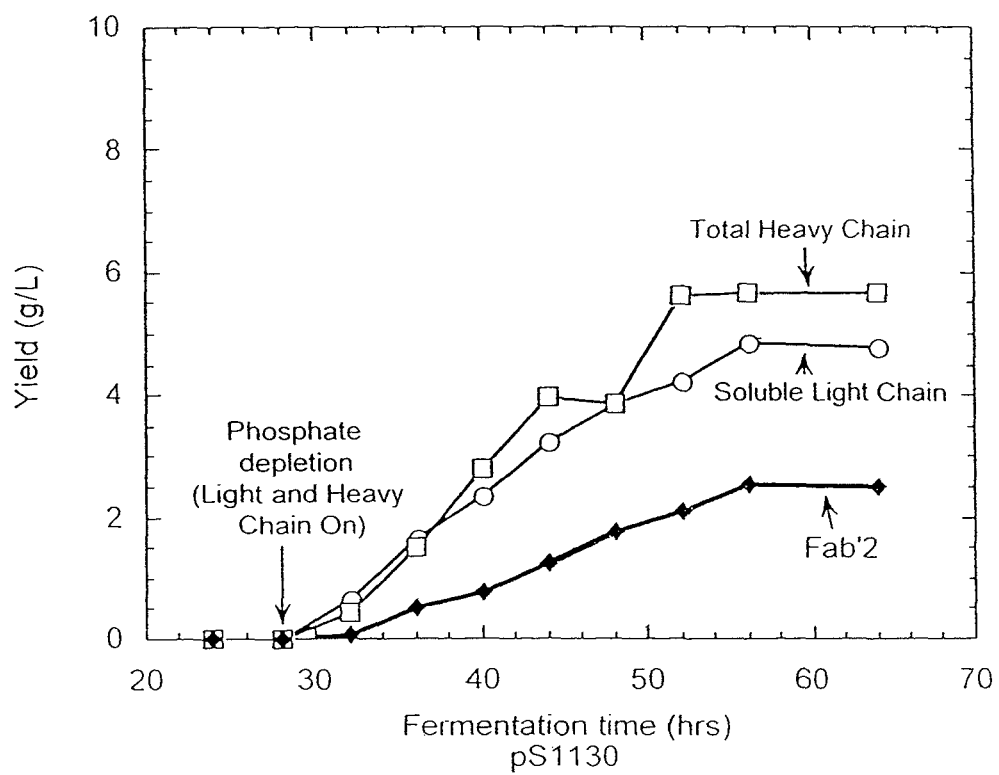
FIG. 5 depicts anti-CD18 expression profiles with the single promoter expression system (pS1130).
Figure 6:
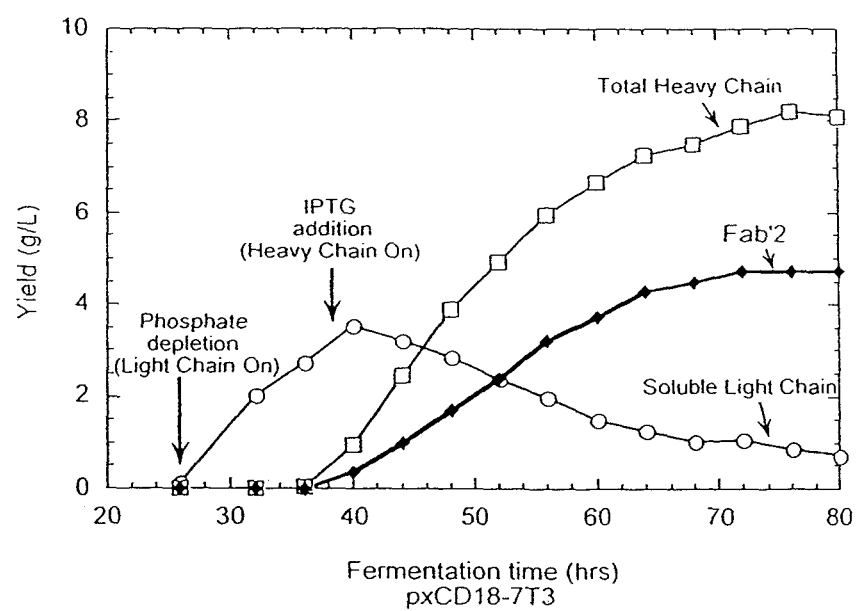
FIG. 6 depicts anti-CD18 expression profiles with the dual-promoter expression system (pxCD18-7T3).

To further illustrate the improved properties of the dual-promoter system, profiles of the expression of total heavy chain, soluble light chain and assembled F(ab')$_2$ complex were established for the single promoter system (pS 1130/ 59A7) and the dual-promoter system (pxCD18-7T3/59A7), the results shown in FIGS. 5 and 6, respectively. Significantly, in the dual-promoter system wherein the light chain was first expressed and secreted into the periplasmic space, followed by a prolonged period of heavy chain production, F(ab')$_2$ assembly occurred almost immediately following the induction of heavy chain expression (FIG. 6); whilst in the single promoter system, the initial F(ab')$_2$ assembly following the induction of both light and heavy chains was relatively poor (FIG. 5). Without intending to be bound by one particular theory, these results suggest that F(ab')$_2$ assembly is inefficient until significant levels of soluble light chain accumulated in the periplasm.

Figure 7:
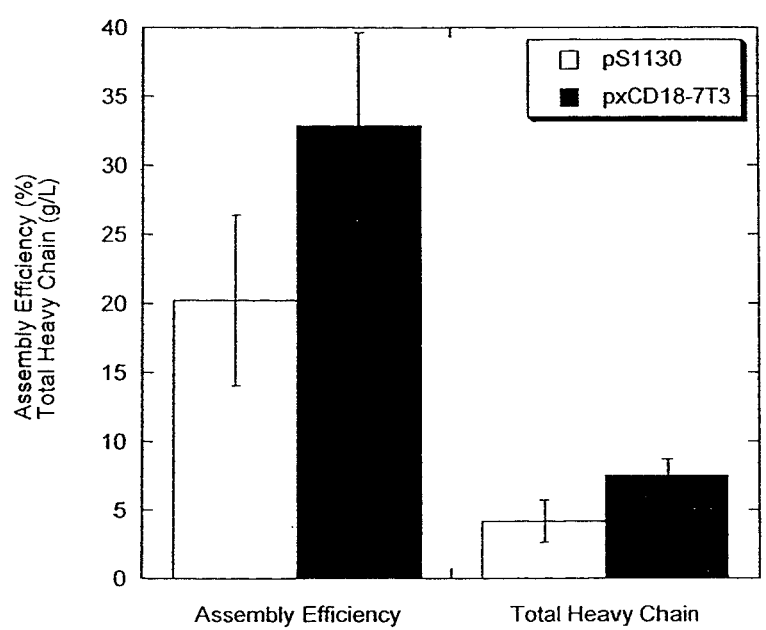
FIG. 7 compares the total heavy chain yields and assembly efficiencies of the single promoter system (pS1130) and the dual promoter system (pxCD18-7T3). The assembly efficiencies represent the fraction of heavy chain assembled into F(ab')$_2$ during the first 10 hours of heavy chain synthesis.

The two systems were further compared for their assembly efficiency, which is defined as the ratio of heavy chain in F(ab')$_2$ complex to the total quantity of heavy chain synthesized. As shown in FIG. 7, the dual-promoter system provides an increased assembly efficiency compared to the traditional single promoter system, particularly during the initial period (first 10 hours) of heavy chain synthesis. A comparison of the heavy chain expression levels of the two systems shows that use of the dual-promoter system also increased the total quantity of heavy chain synthesized, as demonstrated in FIG. 7.

Therefore, the results show that by temporally separating the light and heavy chain synthesis, a significantly increased yield of assembled anti-CD18 F(ab')$_2$ was obtained. The novel system and observations have broad applications in other systems in which multiple protein units are to be expressed and assembled.

Example 2

Production of Anti-Tissue Factor IgG1

This example illustrates the continuing efforts in producing full length antibodies in an *E. coli* system. When both light and full-length heavy chains were co-expressed simultaneously using strong TIR's, a significant amount of expressed precursor polypeptides accumulated, resulting in less quantity of mature light and heavy chains and properly assembled full length antibodies. This example shows that precursor accumulation can be overcome by temporally separating the expression of light and heavy chains. Placing each chain under the control of a different promoter averts the secretory block by allowing for the expression of each chain at separate times. This approach permits the use of stronger TIR's than can be used for simultaneous expression, potentially resulting in a higher level of secretion for each chain. Such expression constructions with higher expression level of individual chains are advantageous for improving yields of full length, properly assembled antibodies.

Materials & Methods

Plasmid Construction

The expression cassette for the control plasmid, paTF130, comprises, from 5' to 3': (1) a phoA promoter (Kikuchi et al., *Nucleic Acids Res.* 9(21):5671-5678 (1981)); (2) trp Shine-Dalgarno (Yanofsky et al., *Nucleic Acids Res.* 9:6647-6668 (1981)); (3) a TIR variant of the STII signal sequence (TIR relative strength ~7) (Simmons and Yansura, *Nature Biotechnology* 14:629-634 (1996)); (4) coding sequence for anti-tissue factor light chain; (5) $\lambda t_o$ terminator (Scholtissek and Grosse, *Nucleic Acids Res.* 15:3185 (1987)); (6) a second phoA promoter; (7) a second trp Shine-Dalgarno; (8) a second silent codon variant of the STII signal sequence (TIR relative strength ~3); (9) coding sequence for anti-tissue factor full-length heavy chain; and (10) a second $\lambda t_o$ terminator. This expression cassette was cloned into the framework of the *E. coli* plasmid pBR322. Sutcliffe (1978) *Cold Spring Harbor Symp. Quant. Biol.* 43:77-90. Thus, the independent transcription of light chain from heavy chain is achieved in this plasmid by placing each gene under the control of its own phoA promoter; however, since both phoA promoters are inducible under identical conditions, both chains are expressed simultaneously.

Alternatively, the vector design of pxTF-7T3FL allows for the temporally separate expression of each chain by using two different, rather than two identical, promoters. In this plasmid, light chain remains under the control of the phoA promoter. However, the tacII promoter (DeBoer, et. al., *Proc. Natl. Acad. Sci. USA* 80:21-25 (1983)) is used to control the transcription of heavy chain. As known in the art, phoA and tacII promoters are induced under substantially different conditions. A schematic comparison of paTF130 and pxTF-7T3FL is depicted in FIG. 8. The nucleic acid sequence of pxTF-7T3FL and the polypeptide sequences it encodes are provided in FIG. 9 and FIG. 10, respectively.

Expression Induction, Sample Preparation and Analysis

For the small scale expression of each construct, *E. coli* strain 33D3, with genotype (W3110 kan$^R$ ΔfhuA (ΔtonA) ptr3 phoAΔE15 lacIq lacL8 ompT Δ(nmpc-fepE) deg P) was used as host cells. Following transformation, selected transformant picks were inoculated into 5 ml Luria-Bertani medium supplemented with carbenicillin (50 ug/ml) and grown at 30° C. on a culture wheel overnight. Each culture was then diluted (1:50) into C.R.A.P. phosphate-limiting media (3.57 g (NH4)2SO4, 0.71 g NaCitrate-2H2O, 1.07 g KCl, 5.36 g Yeast Extract (certified), 5.36 g HycaseSF-Sheffield, adjusted pH with KOH to 7.3, qs to 872 ml with SQ H2O and autoclaved; cooled to 55° C. and supplemented with 110 ml 1M MOPS pH 7.3, 11 ml 50% glucose, 7 ml 1M MgSO4). Carbenicillin was then added to the induction culture at a concentration of 50 ug/ml and, unless otherwise noted, all shake flask inductions were performed in a 2 ml volume.

Following inoculation into the induction medium, the conditions were varied for each sample depending on the promoters used and the timing of promoter induction. For paTF130, the vector using phoA promoters to control the transcription of both light and heavy chain genes, the induction was carried out at 30° C. with shaking for ~24 hours with no other additions made to the culture. Sufficient depletion of the phosphate in this sample leads to the simultaneous induction of the phoA promoters controlling both light and heavy chain transcription. For pxTF-7T3FL, the vector using phoA promoter to control the light chain expression but a tacII promoter to control the heavy chain expression, the induction was first carried out in the same culture conditions as used for paTF130. After ~16 hours with shaking at 30° C., potassium phosphate buffer (pH 7.4) was added to a final concentration of 1 mM. Approximately 45 minutes later, IPTG was added to the culture to a final concentration of 1 mM to induce the tacII promoter. The induction was then continued for another ~8 hours with shaking at 30° C. Thus, paTF130 system represents circumstances in which the transcription of both light chain and heavy chain are simultaneously induced. On the other hand, the pxTF-7T3FL system was cultured under conditions designed to temporally separate the expression of each chain by first inducing the phoA promoter, controlling light chain transcription, and then at a later time inducing the tacII promoter, controlling heavy chain transcription.

Non-reduced whole cell lysates from induced cultures were prepared as follows: (1) 1 OD$_{600}$-ml pellets were centrifuged in a microfuge tube; (2) each pellet was resuspended in 90 ul TE (10 mM Tris pH 7.6. 1 mM EDTA); (3) 10 ul of 100 mM iodoacetic acid (Sigma I-2512) was added to each sample to block any free cysteines and prevent disulfide shuffling; (4) 20 ul of 10% SDS was added to each sample. The samples were vortexed, heated to about 90° C. for ~3 minutes and then vortexed again. After the samples had cooled to room temperature, ~750 ul acetone was added to precipitate the protein. The samples were vortexed and left at room temperature for about 15 minutes. Following centrifugation for 5 minutes in a microcentrifuge, the supernatant of each sample was aspirated off and each protein pellet was resuspended in 50 ul dH$_2$0+50 ul 2×NOVEX sample buffer. The samples were then heated for ~3-5 minutes at about 90° C., vortexed well and allowed to cool to room temperature. A final 5 minute centrifugation was then done and the supernatants were transferred to clean tubes.

Reduced samples were prepared by following steps similar to what is described above for non-reduced samples, except that 10 ul of 1 M DTT was added to the cell resuspension solution in Step (2) and the addition of IAA was omitted in Step (3). Reducing agent was also added to a concentration of 100 mM when the protein precipitate was resuspended in 2× sample buffer+dH$_2$O.

Following preparation, 5 ul of each sample was loaded onto a 10 well, 1.0 mm NOVEX manufactured 12% Tris-Glycine SDS-PAG and electrophoresed at ~120 volts for 1.5-2 hours. The resulting gels were used for immunoblot analysis.

For immunoblot analysis, the SDS-PAGE gels were electroblotted onto nitrocellulose membranes (NOVEX). The membranes were then blocked using a solution of 1×NET (150 mM NaCl, 5 mM EDTA, 50 mM Tris pH 7.4, 0.05% Triton X-100)+0.5% gelatin for approximately 30 min.-1 hour rocking at room temperature. Following the blocking step, the membranes were placed in a solution of 1×NET+ 0.5% gelatin+anti-Fab antibody (peroxidase-conjugated goat IgG fraction to human IgG Fab; CAPPEL #55223) for non-reduced samples or 1×NET+0.5% gelatin+anti-Fab antibody+anti-Fc antibody (Jackson Immuno Research Labs #109-035-008) for reduced samples. The anti-Fab antibody dilution ranged from 1:50,000 to 1:1,000,000 depending on the lot of antibody and the anti-Fc antibody was diluted 1:1,000,000. The membranes were left in the antibody solution overnight at room temperature with rocking. The next morning, the membranes were washed a minimum of 3×10 minutes in 1×NET+0.5% gelatin and then 1×15 minutes in TBS (20 mM Tris pH 7.5, 500 mM NaCl). The protein bands bound by the antibody were visualized by using Amersham Pharmacia. Biotech ECL detection and exposing the membrane to X-Ray film.

Results

Figure 11:
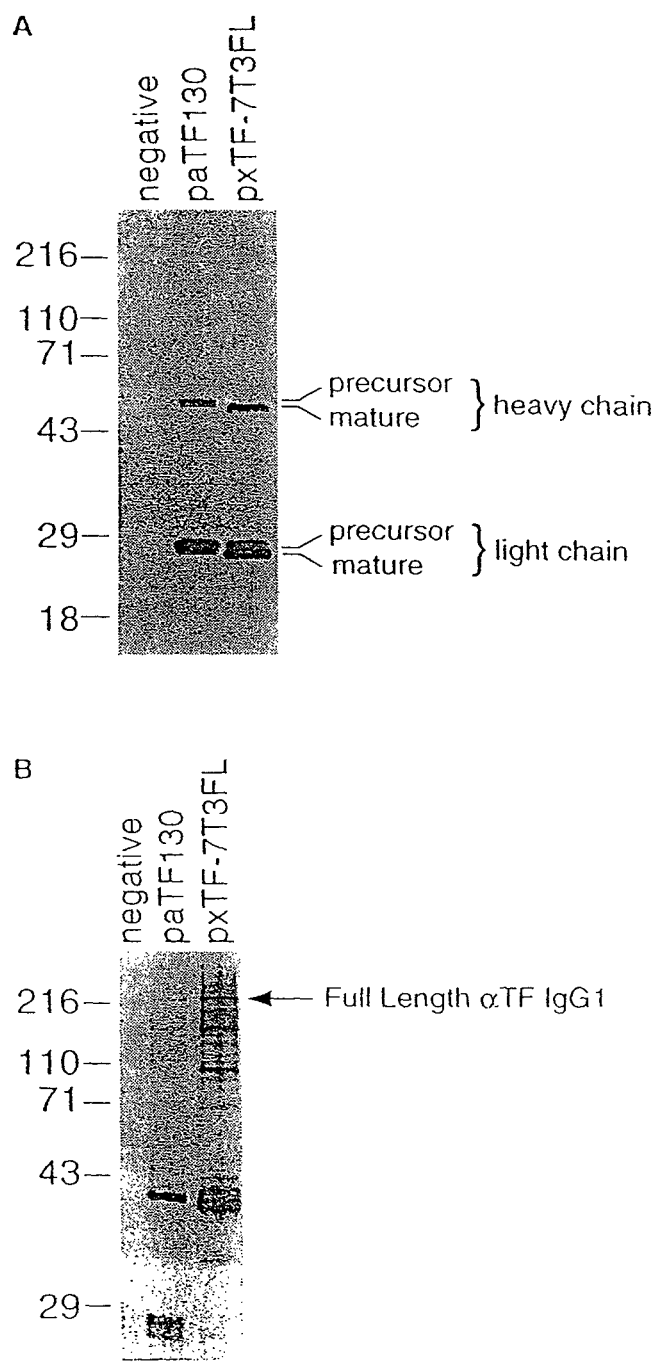
FIGS. 11A and 11B are results of western blots under reduced (11A) or non-reduced (11B) conditions, comparing the anti-Tissue Factor IgG1 expressions using the same promoter system (PhoA/PhoA) and the dual-promoter system (PhoA/TacII).

Plasmids for production of anti-tissue factor IgG1, paTF130 and pxTF-7T3FL, were constructed, transformed into strain 33D3 and induced as previously described. Non-reduced and reduced whole cell lysate samples were then prepared and analyzed by immunoblot. The results are shown in FIG. 11A and FIG. 11B. Using TIR's of 7 for light chain and 3 for heavy chain, a simultaneous induction of the promoters controlling these genes results in a secretory block as demonstrated by the reduced sample for paTF130 (FIG. 11A). The accumulation of both heavy and light chain precursors is clearly evident in this lane. Very little mature light chain and mature heavy chain are detected and the majority of the protein accumulates as precursor. However, once the expression of heavy and light chain are temporally separated, as in pxTF-7T3FL, a significant quantity of mature light chain accumulates (FIG. 11A). Although a small amount of light chain precursor is still detected in this sample, this level does not appear to cause problems for either light chain or heavy chain secretion. In addition, temporal expression leads to the efficient secretion of mature heavy chain, to a significantly greater level than that obtained with paTF130, with no evidence of precursor accumulation.

The correlation of efficient secretion with assembly of the full-length antibody is shown by the non-reduced samples (FIG. 11B). Full-length antibody is detected in both samples; however, the quantity varies dramatically. As the arrow indicates, only a faint full-length band is detected in the paTF130 sample. This band becomes much more prominent in the pxTF-7T3FL sample.

Example 3

Production of Anti-Tissue Factor F(ab')$_2$

In this example, a single promoter plasmid, pCYC56, was used as a control. pCYC56 is structurally analogous to pS 1130. with the exception that the insert sequence encodes for the light and heavy chain fragment of an anti-Tissue Factor antibody. A dual promoter plasmid, pxTF-7T3, was created similar to the dual promoter plasmid pxCD18-7T3 of Example 1, and used to enable temporal separation of anti-Tissue Factor light chain and heavy chain expression. The lacI sequence from the plasmid pMS421 was also incorporated onto pxTF-7T3 to create a new dual promoter pJVG3IL. The addition of lacI obviates the need for co-expression with pMS421.

The host strain used in these fermentations was a derivative of *E. coli* W3110, designated 60H4. The complete genotype of 60H4 is: W3110 ΔfhuAΔmanA phoAΔE15 Δ(argF-lac)169 deoC2 degP41 (ΔpstI-Kan$^r$) IN(rrnD-rrnE) 1 ilvG2096(Val$^r$) Δprc prc-suppressor. The 60H4 host cells were transformed with either pCYC56, pJVG31L or the combination of pxTF-7T3 and pMS421 and successful transformants were selected and grown in culture.

Fermentations were run under conditions similar to those for anti-CD18 F(ab')$_2$ as described in Example 1, with the principle exceptions that the run length varied between approximately 72 and 114 hours, and heavy chain was induced using IPTG from approximately 4 to 12 hours following the attainment of a culture OD550 of 220.

The protein G assay used for anti-CD18 F(ab')$_2$ was also used to analyze the anti-Tissue Factor F(ab')$_2$ products, with the exception that an anti-Tissue Factor F(ab')$_2$ standard was used to generate the standard curve.

A series of anti-Tissue Factor F(ab')$_2$ fermentation runs were conducted using the promoter systems described above. The yields of assembled anti-Tissue Factor F(ab')$_2$ complex increased from 1 g/L with the single promoter system to 2.6±0.3 g/L (n=13) using the dual promoter system with pJVG31L.

Therefore, the results show that by temporally separating the light and heavy chain synthesis, a significantly increased yield of assembled anti-Tissue Factor F(ab')$_2$ was obtained.

Although the forgoing refers to particular embodiments, it will be understood that the present invention is not so limited. It will occur to those ordinary skilled in the art that various modifications may be made to the disclosed embodiments without diverting from the overall concept of the invention. All such modifications are. intended to be within the scope of the present invention.

What is claimed is:

1. A process for producing a functional antibody or fragment thereof in a host cell transformed with two separate translational units respectively encoding the light and heavy chains of said antibody or fragment thereof, comprising the steps of: a) culturing the host cell and expressing the light chain for a period of time before the heavy chain is expressed, thereby temporally separating the production of the light and heavy chains; and b) allowing the assembly of the light and heavy chains to form the functional antibody or fragment thereof, wherein the antibody fragment is selected from the group consisting of Fab, Fab', F(ab')$_2$, F(ab')$_2$-leucine zipper, Fv and dsFv.

2. The process of claim 1 wherein the host cell is prokaryotic, each translational unit further comprising a nucleotide sequence encoding for a prokaryotic secretion signal operably linked to the N'-terminal of the light or heavy chain.

3. The process of claim 2, wherein the two separate translational units are controlled by different promoters.

4. The process of claim 3, wherein the two translational units are located on a single recombinant vector.

5. The process of claim 2, wherein the secretion signal is selected from the group consisting of STII, OmpA, PhoE, LamB, MBP and PhoA.

6. The process of claim 5, wherein the secretion signal is STII.

7. The process of claim 3, wherein the promoter for the translational unit encoding the light chain is selected from the group consisting of phoA and trp, and wherein the promoter for the translational unit encoding the heavy chain is selected from the group consisting of trc, TacI, TacII, lpp, lac-lpp, lac, ara, and T7.

8. The process of claim 7, wherein the promoter for the translational unit encoding the light chain is the phoA promoter and the promoter for the translational unit encoding the heavy chain is the TacII promoter.

9. The process of claim 1, wherein the antibody is specific to an antigen selected from the group consisting of VEGF, IgE, CD11, CD18 and tissue factor (TF).

10. The process of claim 9, wherein the antibody is an anti-CD18 antibody or an anti-TF antibody.

11. The process of claim 1, wherein the antibody is a chimeric antibody.

12. The process of claim 1, wherein the antibody is a humanized antibody.

13. The process of claim 1, wherein the antibody is a human antibody.

14. The process of claim 1, wherein the host cell is a prokaryotic cell from an *E. coli* strain.

15. The process of claim 14, wherein the *E. coli* strain is genetically engineered to over-express at least one chaperone protein selected from the group consisting of DsbA, DsbC, DsbG and FkpA.

16. The process of claim 14, wherein the *E. coli* strain is deficient for endogenous protease activities.

17. The process of claim 14, wherein the genotype of the *E. coli* strain contains Δprc prc-suppressor.

18. The process of claim 1, wherein the heavy chain of the antibody is full length.

* * * * *

SEQUENCE LISTING

<160> NUMBER OF SEQ ID NOS: 6

<210> SEQ ID NO 1
<211> LENGTH: 237
<212> TYPE: PRT
<213> ORGANISM: Artificial sequence
<220> FEATURE:
<223> OTHER INFORMATION: Synthetic construct

<400> SEQUENCE: 1

```
Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Gln Asp Ile Asn Asn Tyr Leu Asn Trp Tyr Gln Gln Lys Pro Gly
    50                  55                  60

Lys Ala Pro Lys Leu Leu Ile Tyr Tyr Thr Ser Thr Leu His Ser Gly
65                  70                  75                  80

Val Pro Ser Arg Phe Ser Gly Ser Gly Ser Gly Thr Asp Tyr Thr Leu
                85                  90                  95

Thr Ile Ser Ser Leu Gln Pro Glu Asp Phe Ala Thr Tyr Tyr Cys Gln
            100                 105                 110

Gln Gly Asn Thr Leu Pro Pro Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 2
<211> LENGTH: 300
<212> TYPE: PRT
<213> ORGANISM: Artificial sequence
<220> FEATURE:
<223> OTHER INFORMATION: Synthetic construct

<400> SEQUENCE: 2

```
Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
            20                  25                  30

Gly Leu Val Gln Pro Gly Gly Ser Leu Arg Leu Ser Cys Ala Thr Ser
        35                  40                  45

Gly Tyr Thr Phe Thr Glu Tyr Thr Met His Trp Met Arg Gln Ala Pro
    50                  55                  60

Gly Lys Gly Leu Glu Trp Val Ala Gly Ile Asn Pro Lys Asn Gly Gly
65                  70                  75                  80

Thr Ser His Asn Gln Arg Phe Met Asp Arg Phe Thr Ile Ser Val Asp
                85                  90                  95

Lys Ser Thr Ser Thr Ala Tyr Met Gln Met Asn Ser Leu Arg Ala Glu
            100                 105                 110

Asp Thr Ala Val Tyr Tyr Cys Ala Arg Trp Arg Gly Leu Asn Tyr Gly
```

```
            115                 120                 125
Phe Asp Val Arg Tyr Phe Asp Val Trp Gly Gln Gly Thr Leu Val Thr
            130                 135                 140
Val Ser Ser Ala Ser Thr Lys Gly Pro Ser Val Phe Pro Leu Ala Pro
145                 150                 155                 160
Ser Ser Lys Ser Thr Ser Gly Gly Thr Ala Ala Leu Gly Cys Leu Val
                165                 170                 175
Lys Asp Tyr Phe Pro Glu Pro Val Thr Val Ser Trp Asn Ser Gly Ala
            180                 185                 190
Leu Thr Ser Gly Val His Thr Phe Pro Ala Val Leu Gln Ser Ser Gly
            195                 200                 205
Leu Tyr Ser Leu Ser Ser Val Val Thr Val Pro Ser Ser Ser Leu Gly
        210                 215                 220
Thr Gln Thr Tyr Ile Cys Asn Val Asn His Lys Pro Ser Asn Thr Lys
225                 230                 235                 240
Val Asp Lys Lys Val Glu Pro Lys Ser Cys Asp Lys Thr His Thr Cys
                245                 250                 255
Pro Pro Cys Pro Ala Pro Glu Leu Leu Gly Gly Arg Met Lys Gln Leu
            260                 265                 270
Glu Asp Lys Val Glu Glu Leu Leu Ser Lys Asn Tyr His Leu Glu Asn
            275                 280                 285
Glu Val Ala Arg Leu Lys Lys Leu Val Gly Glu Arg
        290                 295                 300

<210> SEQ ID NO 3
<211> LENGTH: 2700
<212> TYPE: DNA
<213> ORGANISM: Artificial sequence
<220> FEATURE:
<223> OTHER INFORMATION: Synthetic construct

<400> SEQUENCE: 3
gaattcaact tctccatact ttggataagg aaatacagac atgaaaaatc tcattgctga     60
gttgttattt aagcttgccc aaaaagaaga agagtcgaat gaactgtgtg cgcaggtaga    120
agctttggag attatcgtca ctgcaatgct tcgcaatatg gcgcaaaatg accaacagcg    180
gttgattgat caggtagagg gggcgctgta cgaggtaaag cccgatgcca gcattcctga    240
cgacgatacg gagctgctgc gcgattacgt aaagaagtta ttgaagcatc ctcgtcagta    300
aaaagttaat cttttcaaca gctgtcataa agttgtcacg gccgagactt atagtcgctt    360
tgtttttatt tttaatgta tttgtaacta gtacgcaagt tcacgtaaaa agggtatcta    420
gaattatgaa aagaatatc gcatttcttc ttgcatctat gttcgttttt tctattgcta    480
caaacgcgta cgctgatatc cagatgaccc agtccccgag ctccctgtcc gcctctgtgg    540
gcgatagggt caccatcacc tgtcgtgcca gtcaggacat caacaattat ctgaactggt    600
atcaacagaa accaggaaaa gctccgaaac tactgattta ctatacctcc accctccact    660
ctggagtccc ttctcgcttc tctggttctg gttctggac ggattacact ctgaccatca    720
gcagtctgca accggaggac ttcgcaactt attactgtca gcaaggtaat actctgccgc    780
cgacgttcgg acagggcacg aaggtggaga tcaaacgaac tgtggctgca ccatctgtct    840
tcatcttccc gccatctgat gagcagttga aatctggaac tgcctctgtt gtgtgcctgc    900
tgaataactt ctatcccaga gaggccaaag tacagtggaa ggtggataac gccctccaat    960
cgggtaactc ccaggagagt gtcacagagc aggacagcaa ggacagcacc tacagcctca   1020
```

```
gcagcaccct gacgctgagc aaagcagact acgagaaaca caagtctac gcctgcgaag    1080 tcacccatca gggcctgagc tcgcccgtca caaagagctt caacagggga gagtgttaat    1140
taaatcctct acgccggacg catcgtggcg agctcggtac ccggggatct aggcctaacg    1200
ctcggttgcc gccgggcgtt ttttattgtt gccgacgcgc atctcgactg cacggtgcac    1260
caatgcttct ggcgtcaggc agccatcgga agctgtggta tggctgtgca ggtcgtaaat    1320
cactgcataa ttcgtgtcgc tcaaggcgca ctcccgttct ggataatgtt ttttgcgccg    1380
acatcataac ggttctggca atattctga aatgagctgt tgacaattaa tcatcgaact    1440
agtttaatgt gtggaattgt gagcggataa caattaagct taggatctag aattatgaag    1500
aagaatattg cgttcctact tgcctctatg tttgtctttt ctatagctac aaacgcgtac    1560
gctgaggttc agctggtgga gtctggcggt ggcctggtgc agccaggggg ctcactccgt    1620
ttgtcctgtg caacttctgg ctacaccttt accgaataca ctatgcactg gatgcgtcag    1680
gccccgggta agggcctgga atgggttgca gggattaatc ctaaaaacgg tggtaccagc    1740
cacaaccaga ggttcatgga ccgtttcact ataagcgtag ataaatccac cagtacagcc    1800
tacatgcaaa tgaacagcct gcgtgctgag gacactgccg tctattattg tgctagatgg    1860
cgaggcctga actacggctt tgacgtccgt tattttgacg tctggggtca aggaaccctg    1920
gtcaccgtct cctcggcctc caccaagggc ccatcggtct tccccctggc accctcctcc    1980
aagagcacct ctgggggcac agcggccctg ggctgcctgg tcaaggacta cttccccgaa    2040
ccggtgacgg tgtcgtggaa ctcaggcgcc ctgaccagcg gcgtgcacac cttcccggct    2100
gtcctacagt cctcaggact ctactccctc agcagcgtgg tgaccgtgcc ctccagcagc    2160
ttgggcaccc agacctacat ctgcaacgtg aatcacaagc ccagcaacac caaggtcgac    2220
aagaaagttg agcccaaatc ttgtgacaaa actcacacat gcccgccgtg cccagcacca    2280
gaactgctgg gcggccgcat gaaacagcta gaggacaagg tcgaagagct actctccaag    2340
aactaccacc tagagaatga agtggcaaga ctcaaaaagc ttgtcgggga gcgctaagca    2400
tgcgacggcc ctagagtccc taacgctcgg ttgccgccgg gcgttttttta tgttaactc    2460 atgtttgaca gcttatcatc gataagcttt aatgcggtag tttatcacag ttaaattgct    2520
aacgcagtca ggcaccgtgt atgaaatcta acaatgcgct catcgtcatc ctcggcaccg    2580
tcaccctgga tgctgtaggc ataggcttgg ttatgccggt actgccgggc ctcttgcggg    2640
atatcgtcca ttccgacagc atcgccagtc actatggcgt gctgctagcg ctatatgcgt    2700
```

<210> SEQ ID NO 4
<211> LENGTH: 237
<212> TYPE: PRT
<213> ORGANISM: Artificial sequence
<220> FEATURE:
<223> OTHER INFORMATION: Synthetic construct

<400> SEQUENCE: 4

Met Lys Lys Asn Ile Ala Phe Leu Leu Ala Ser Met Phe Val Phe Ser
 1               5                  10                  15

Ile Ala Thr Asn Ala Tyr Ala Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Arg Asp Ile Lys Ser Tyr Leu Asn Trp Tyr Gln Gln Lys Pro Gly
    50                  55                  60

Lys Ala Pro Lys Val Leu Ile Tyr Tyr Ala Thr Ser Leu Ala Glu Gly

-continued

```
                65                  70                  75                  80
Val Pro Ser Arg Phe Ser Gly Ser Gly Ser Gly Thr Asp Tyr Thr Leu
                        85                  90                  95

Thr Ile Ser Ser Leu Gln Pro Glu Asp Phe Ala Thr Tyr Tyr Cys Leu
                        100                 105                 110

Gln His Gly Glu Ser Pro Trp Thr Phe Gly Gln Gly Thr Lys Val Glu
                        115                 120                 125

Ile Lys Arg Thr Val Ala Ala Pro Ser Val Phe Ile Phe Pro Pro Ser
                        130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                        165                 170                 175

Leu Gln Ser Gly Asn Ser Gln Glu Ser Val Thr Glu Gln Asp Ser Lys
                        180                 185                 190

Asp Ser Thr Tyr Ser Leu Ser Ser Thr Leu Thr Leu Ser Lys Ala Asp
                        195                 200                 205

Tyr Glu Lys His Lys Val Tyr Ala Cys Glu Val Thr His Gln Gly Leu
                        210                 215                 220

Ser Ser Pro Val Thr Lys Ser Phe Asn Arg Gly Glu Cys
225                 230                 235
```

<210> SEQ ID NO 5
<211> LENGTH: 470
<212> TYPE: PRT
<213> ORGANISM: Artificial sequence
<220> FEATURE:
<223> OTHER INFORMATION: Synthetic construct

<400> SEQUENCE: 5

```
Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
                20                  25                  30

Gly Leu Val Gln Pro Gly Gly Ser Leu Arg Leu Ser Cys Ala Ala Ser
            35                  40                  45

Gly Phe Asn Ile Lys Glu Tyr Tyr Met His Trp Val Arg Gln Ala Pro
        50                  55                  60

Gly Lys Gly Leu Glu Trp Val Gly Leu Ile Asp Pro Glu Gln Gly Asn
65                  70                  75                  80

Thr Ile Tyr Asp Pro Lys Phe Gln Asp Arg Ala Thr Ile Ser Ala Asp
                85                  90                  95

Asn Ser Lys Asn Thr Ala Tyr Leu Gln Met Asn Ser Leu Arg Ala Glu
                100                 105                 110

Asp Thr Ala Val Tyr Tyr Cys Ala Arg Asp Thr Ala Ala Tyr Phe Asp
            115                 120                 125

Tyr Trp Gly Gln Gly Thr Leu Val Thr Val Ser Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
```

```
            195                 200                 205
Val Thr Val Pro Ser Ser Leu Gly Thr Gln Thr Tyr Ile Cys Asn
    210                 215                 220

Val Asn His Lys Pro Ser Asn Thr Lys Val Asp Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 6
<211> LENGTH: 3100
<212> TYPE: DNA
<213> ORGANISM: Artificial sequence
<220> FEATURE:
<223> OTHER INFORMATION: Synthetic construct

<400> SEQUENCE: 6
gaattcaact tctccatact ttggataagg aaatacagac atgaaaaatc tcattgctga      60
gttgttattt aagcttgccc aaaaagaaga gagtcgaat gaactgtgtg cgcaggtaga     120
agctttggag attatcgtca ctgcaatgct tcgcaatatg gcgcaaaatg accaacagcg     180
gttgattgat caggtagagg gggcgctgta cgaggtaaag cccgatgcca gcattcctga     240
cgacgatacg gagctgctgc gcgattacgt aaagaagtta ttgaagcatc ctcgtcagta     300
aaaagttaat ctttttcaaca gctgtcataa agttgtcacg gccgagactt atagtcgctt     360 tgttttttatt ttttaatgta tttgtaacta gtacgcaagt tcacgtaaaa agggtatcta     420
gaattatgaa aagaatatc gcatttcttc ttgcatctat gttcgttttt tctattgcta     480
```

```
caaacgcgta cgctgatatc cagatgaccc agtccccgag ctccctgtcc gcctctgtgg    540
gcgatagggt caccatcacc tgcagagcca gtcgcgacat caagagctat ctgaactggt    600
atcaacagaa accaggaaaa gctccgaaag tactgattta ctatgctact agtctcgctg    660
aaggagtccc ttctcgcttc tctggatccg gttctgggac ggattacact ctgaccatca    720
gcagtctgca gccagaagac ttcgcaactt attactgtct tcagcacgga gagtctccat    780
ggacatttgg acagggtacc aaggtggaga tcaaacgaac tgtggctgca ccatctgtct    840
tcatcttccc gccatctgat gagcagttga aatctggaac tgcttctgtt gtgtgcctgc    900
tgaataactt ctatcccaga gaggccaaag tacagtggaa ggtggataac gccctccaat    960
cgggtaactc ccaggagagt gtcacagagc aggacagcaa ggacagcacc tacagcctca   1020
gcagcaccct gacgctgagc aaagcagact acgagaaaca caaagtctac gcctgcgaag   1080
tcacccatca gggcctgagc tcgcccgtca caaagagctt caacagggga gagtgttaat   1140
taaatcctct acgccggacg catcgtggcg agctcggtac ccggggatct aggcctaacg   1200
ctcggttgcc gccgggcgtt ttttattgtt gccgacgcgc atctcgactg cacggtgcac   1260
caatgcttct ggcgtcaggc agccatcgga gctgtggta tggctgtgca ggtcgtaaat   1320
cactgcataa ttcgtgtcgc tcaaggcgca ctcccgttct ggataatgtt ttttgcgccg   1380
acatcataac ggttctggca atattctga atgagctgt tgacaattaa tcatcgaact   1440
agtttaatgt gtgaattgt gagcggataa caattaagct taggatctag aattatgaag   1500
aagaatattg cgttcctact tgcctctatg tttgtctttt ctatagctac aaacgcgtac   1560
gctgaggttc agctggtgga gtctggcggt ggcctggtgc agccagggg ctcactccgt   1620 ttgtcctgtg cagcttctgg cttcaatatt aaggagtact acatgcactg gtccgtcag   1680 gccccgggta agggcctgga atgggttgga ttgattgatc cagagcaagg caacacgatc   1740
tatgacccga gttccagga ccgtgccact ataagcgctg acaattccaa aaacacagca   1800
tacctgcaga tgaacagcct gcgtgctgag gacactgccg tctattattg tgctcgagac   1860
acggccgctt acttcgacta ctgggggtcaa ggaaccctgg tcaccgtctc ctcggcctcc   1920
accaagggcc catcggtctt ccccctggca cctcctcca agagcacctc tgggggcaca   1980
gcggccctgg gctgcctggt caaggactac ttccccgaac cggtgacggt gtcgtggaac   2040
tcaggcgccc tgaccagcgg cgtgcacacc ttcccggctg tcctacagtc ctcaggactc   2100
tactccctca gcagcgtggt gactgtgccc tctagcagct gggcaccca gacctacatc   2160 tgcaacgtga atcacaagcc cagcaacacc aaggtggaca gaaagttga gcccaaatct   2220 tgtgacaaaa ctcacacatg cccaccgtgc ccagcacctg aactcctggg gggaccgtca   2280
gtcttcctct ttccccccaaa acccaaggac accctcatga tctcccggac ccctgaggtc   2340
acatgcgtgg tggtggacgt gagccacgaa gaccctgagg tcaagttcaa ctggtacgtg   2400
gacggcgtgg aggtgcataa tgccaagaca aagccgcggg aggagcagta caacagcacg   2460
taccgtgtgg tcagcgtcct caccgtcctg caccaggact ggctgaatgg caaggagtac   2520
aagtgcaagg tctccaacaa agccctccca gccccatcg agaaaaccat ctccaaagcc   2580
aaagggcagc cccgagaacc acaggtgtac accctgcccc catcccggga agagatgacc   2640
aagaaccagg tcagcctgac ctgcctggtc aaaggcttct atcccagcga catcgccgtg   2700
gagtgggaga gcaatgggca gccggagaac aactacaaga ccacgcctcc cgtgctggac   2760
tccgacggct ccttcttcct ctacagcaag ctcaccgtgg acaagagcag gtggcagcag   2820
gggaacgtct tctcatgctc cgtgatgcat gaggctctgc acaaccacta cacgcagaag   2880
```

-continued

```
agcctctccc tgtctccggg taaataagca tgcgacggcc ctagagtccc taacgctcgg    2940
ttgccgccgg gcgtttttta ttgttaactc atgtttgaca gcttatcatc gataagcttt    3000
aatgcggtag tttatcacag ttaaattgct aacgcagtca ggcaccgtgt atgaaatcta    3060
acaatgcgct catcgtcatc ctcggcaccg tcaccctgga                          3100
```